United States Patent
Dodd et al.

(10) Patent No.: US 12,384,760 B2
(45) Date of Patent: Aug. 12, 2025

(54) SUBSTITUTED CARBAZOLE COMPOUNDS

(71) Applicant: BRISTOL-MYERS SQUIBB COMPANY, Princeton, NJ (US)

(72) Inventors: Dharmpal S. Dodd, Escondido, CA (US); Trevor C. Sherwood, West Windsor, NJ (US); Shoshana L. Posy, Highland Park, NJ (US); Alaric J. Dyckman, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 379 days.

(21) Appl. No.: 17/766,392

(22) PCT Filed: Oct. 2, 2020

(86) PCT No.: PCT/US2020/053886
§ 371 (c)(1),
(2) Date: Apr. 4, 2022

(87) PCT Pub. No.: WO2021/067657
PCT Pub. Date: Apr. 8, 2021

(65) Prior Publication Data
US 2024/0076280 A1   Mar. 7, 2024

Related U.S. Application Data

(60) Provisional application No. 62/910,671, filed on Oct. 4, 2019.

(51) Int. Cl.
| | | |
|---|---|---|
| C07D 401/14 | (2006.01) | |
| C07D 401/04 | (2006.01) | |
| C07D 405/14 | (2006.01) | |
| C07D 413/14 | (2006.01) | |
| C07D 471/04 | (2006.01) | |

(52) U.S. Cl.
CPC ......... *C07D 401/14* (2013.01); *C07D 401/04* (2013.01); *C07D 405/14* (2013.01); *C07D 413/14* (2013.01); *C07D 471/04* (2013.01)

(58) Field of Classification Search
None
See application file for complete search history.

(56) References Cited

U.S. PATENT DOCUMENTS

| | | |
|---|---|---|
| 6,187,777 B1 | 2/2001 | Norman et al. |
| 6,306,874 B1 | 10/2001 | Fraley et al. |
| 6,867,200 B1 | 3/2005 | Allen et al. |
| 7,410,975 B2 | 8/2008 | Lipford et al. |
| 8,138,187 B2 | 3/2012 | Zemolka et al. |
| 8,354,400 B2 | 1/2013 | Zheng et al. |
| 9,126,996 B2 | 9/2015 | Lipford et al. |
| 9,126,999 B2 | 9/2015 | Bolvin et al. |
| 9,241,991 B2 | 1/2016 | Ji et al. |
| 9,353,115 B2 | 5/2016 | Lipford et al. |
| 9,376,398 B2 | 6/2016 | Hori et al. |
| 9,428,495 B2 | 8/2016 | Carlson et al. |
| 9,643,967 B2 | 5/2017 | Koul et al. |
| 2004/0014802 A1 | 1/2004 | Dutruc-Rosset et al. |
| 2006/0235037 A1 | 10/2006 | Purandare et al. |
| 2010/0160314 A1 | 6/2010 | Lipford et al. |
| 2010/0197657 A1 | 8/2010 | Chang et al. |
| 2011/0015219 A1 | 1/2011 | Trawick et al. |
| 2011/0071150 A1 | 3/2011 | Alam et al. |
| 2011/0105427 A1 | 5/2011 | Daun et al. |
| 2011/0183967 A1 | 7/2011 | Zheng et al. |
| 2011/0275631 A1 | 11/2011 | Abeywardane et al. |
| 2013/0045986 A1 | 2/2013 | Nagarathnam et al. |
| 2013/0324547 A1 | 12/2013 | Boivin et al. |
| 2014/0066432 A1 | 3/2014 | Howbert et al. |
| 2014/0088085 A1 | 3/2014 | Burgess et al. |

(Continued)

FOREIGN PATENT DOCUMENTS

| | | | |
|---|---|---|---|
| CN | 109867662 A | * | 6/2019 |
| EP | 2738172 A1 | | 6/2014 |

(Continued)

OTHER PUBLICATIONS

O'Brien. W. et al. Carprofen: A New Nonsteroidal Antiinflammatory Drug. Pharmacotherapy, 1987, 7(1):16-24 (Year: 1987).*
Taechowisan, T. et al. Anti-Inflammatory Effect of 3-Methylcarbazoles on RAW 264.7 Cells Stimulated with LPS, Polyinosinic-Polycytidylic Acid and Pam3CSK. Advances in Microbiology, 2012, 2, 98-103. (Year: 2012).*
International Preliminary Report on Patentability for No. PCT/US2020/053886, issued Apr. 5, 2022.
Kawai, T., et al., "The Role of Pattern-Recognition Receptors in Innate Immunity: Update on Toll-like Receptors", Nature Immunol., 2011, 11, 373-384.
Koolman et al., Novel Syntheses of Variably Substituted Pyrrolo[2,3-d]thiazoles, Synthesis, 2010, No. 18, pp. 3152-3162.
Kutchukian, Peter S. et al., "Chemistry Informer Libraries: a chemoinformatics enabled approach to evaluate and advance synthetic methods", Chemical Science, 2016, vol. 7(4), pp. 2604-2613.

(Continued)

*Primary Examiner* — Clinton A Brooks
*Assistant Examiner* — Nicola Maria Bauer
(74) *Attorney, Agent, or Firm* — Gary Greenblatt

(57) ABSTRACT

Disclosed are compounds of Formula (I) or salts thereof, wherein $R_1$, $R_2$, $R_3$, $R_4$, and $R_5$ are defined herein. Also disclosed are methods of using such compounds as inhibitors of signaling through Toll-like receptor 7, 8, or 9, and pharmaceutical compositions comprising such compounds. These compounds are useful in treating inflammatory and autoimmune diseases.

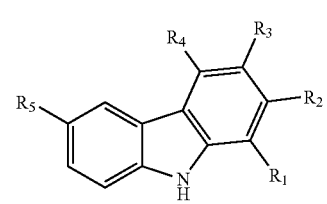

(I)

13 Claims, No Drawings

(56) References Cited

U.S. PATENT DOCUMENTS

| | | |
|---|---|---|
| 2014/0242121 A1 | 8/2014 | Lipford et al. |
| 2015/0214490 A1 | 7/2015 | Kim et al. |
| 2015/0231142 A1 | 8/2015 | Van Goor et al. |
| 2017/0008885 A1 | 1/2017 | Koul et al. |
| 2017/0273983 A1 | 9/2017 | Ding et al. |
| 2018/0000790 A1 | 1/2018 | Dyckman et al. |

FOREIGN PATENT DOCUMENTS

| | | | |
|---|---|---|---|
| WO | 03057696 A1 | 7/2003 | |
| WO | 2006113458 A1 | 10/2006 | |
| WO | 2007000241 A1 | 1/2007 | |
| WO | 2007115306 A2 | 10/2007 | |
| WO | 2008065198 A1 | 6/2008 | |
| WO | 2008152471 A1 | 12/2008 | |
| WO | 2009030996 A1 | 3/2009 | |
| WO | 2010149769 A1 | 12/2010 | |
| WO | WO-2011011186 A2 * | 1/2011 | ........... A61K 31/403 |
| WO | 2013010904 A1 | 1/2013 | |
| WO | 2013181579 A2 | 12/2013 | |
| WO | 2015088045 A1 | 6/2015 | |
| WO | 2016029077 A1 | 2/2016 | |
| WO | 2018005586 A1 | 1/2018 | |
| WO | 2018026620 A1 | 2/2018 | |
| WO | 2018049089 A1 | 3/2018 | |
| WO | 2019099336 A1 | 5/2019 | |
| WO | 2019125977 A1 | 6/2019 | |
| WO | 2019126253 A1 | 6/2019 | |
| WO | WO-2019126113 A1 * | 6/2019 | ........... A61K 31/437 |

OTHER PUBLICATIONS

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. on Therapeutic Patents, 2016, vol. 26, No. 6, 719-730.

Sims, et al., "The IL-1 Family: Regulators of Immunity", Nature Rev. Immunol., 2010, 10, 89-102.

* cited by examiner

SUBSTITUTED CARBAZOLE COMPOUNDS

CROSS REFERENCE

This application is a national phase application under 35 U.S.C. § 371 of International Patent Application No. PCT/US2020/053886, filed Oct. 2, 2020, which claims priority to U.S. Provisional Application Ser. 62/910,671, filed Oct. 4, 2019, the contents of which are specifically incorporated fully herein by reference.

FIELD OF THE INVENTION

The invention generally relates to substituted carbazole compounds, method for preparing these compounds, and their use in the treatment of inflammatory and autoimmune diseases.

BACKGROUND OF THE INVENTION

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., Nature Immunol., 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, J. E. et al., Nature Rev. Immunol., 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7/8/9 are among the set that are endosomally located and respond to single-stranded RNA (TLR7 and TLR8) or unmethylated single-stranded DNA containing cytosine—phosphate—guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

SUMMARY OF THE INVENTION

The present invention relates to a new class of substituted carbazole compounds found to be effective inhibitors of signaling through TLR7/8/9. These compounds are provided to be useful as pharmaceuticals with desirable stability, bioavailability, therapeutic index, and toxicity values that are important to their drugability.

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION OF THE INVENTION

The first aspect of the invention provides at least one compound of Formula (I),

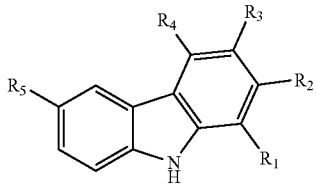
(I)

or a salt thereof, wherein:

$R_1$ is H, R, or —OR;

$R_2$ is —NHC(O)CH$_3$ or a cyclic group selected from:

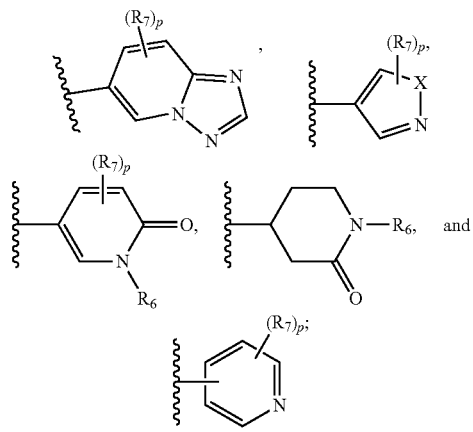

X is O, —NH, or —NR;

$R_3$ and $R_4$ are independently H, R, or —OR;

each R is independently $C_{1-3}$ alkyl;

$R_5$ is:

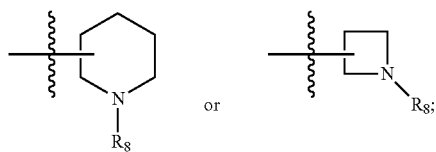

$R_6$ is H or $C_{1-3}$ alkyl;

each $R_7$ is independently $C_{1-3}$ alkyl or $C_{1-3}$ alkoxy;

$R_8$ is H, —CH$_2$CN, —CH$_2$C(CH$_3$)$_2$OH, —C(O)CH$_2$N(CH$_3$)$_2$CH$_2$CH$_2$S(O)$_2$CH$_3$, oxetanyl, or tetrahydropyranyl; and p is zero, 1 or 2.

One embodiment provides a compound of Formula (I) or a salt thereof, wherein $R_1$ is H.

Another embodiment provides a compound of Formula (I) or a salt thereof, wherein $R_2$ is —NHC(O)CH$_3$.

Another embodiment provides a compound of Formula (I) or a salt thereof, wherein $R_2$ is a cyclic group selected from:

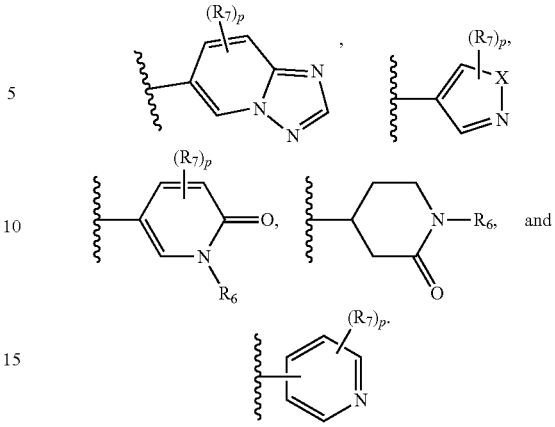

Another embodiment provides a compound of Formula (I) or a salt thereof, wherein X is O.

Yet another embodiment provides a compound of Formula (I) or a salt thereof, wherein X is —NR. Included in this embodiment are compounds in which X is —NCH$_3$.

Another embodiment provides a compound of Formula (I) or a salt thereof, wherein X is —NH.

Another embodiment provides a compound of Formula (I) or a salt thereof, wherein $R_6$ is H.

Another embodiment provides a compound of Formula (I) or a salt thereof, wherein $R_6$ is $C_{1-3}$ alkyl. Also included in this embodiment are compounds in which $R_6$ is —CH$_3$.

Another embodiment provides a compound of Formula (I) or a salt thereof, wherein each $R_7$ is independently $C_{1-3}$ alkyl or $C_{1-3}$ alkoxy.

Another embodiment provides a compound of Formula (I) or a salt thereof, wherein at least one $R_7$ is a $C_{1-3}$ alkyl. Included in this embodiment are compounds in which at least one $R_7$ is —CH$_3$.

Another embodiment provides a compound of Formula (I) or a salt thereof, wherein at least one $R_7$ is a $C_{1-3}$ alkoxy. Included in this embodiment are compounds in which at least one $R_7$ is —OCH$_3$.

One embodiment provides a compound of Formula (I) or a salt thereof, wherein p is zero.

One embodiment provides a compound of Formula (I) or a salt thereof, wherein p is 1.

One embodiment provides a compound of Formula (I) or a salt thereof, wherein p is 2.

Another embodiment provides a compound of Formula (I) or a salt thereof, wherein $R_3$ and $R_4$ are independently H, $C_{1-2}$ alkyl, or $C_{1-2}$ alkoxy.

Another embodiment provides a compound of Formula (I) or a salt thereof, wherein $R_3$ and $R_4$ are independently H, —CH$_3$, or —OCH$_3$.

One embodiment provides a compound of Formula (I) or a salt thereof, wherein $R_3$ is H.

Another embodiment provides a compound of Formula (I) or a salt thereof, wherein $R_3$ is —CH$_3$.

Another embodiment provides a compound of Formula (I) or a salt thereof, wherein $R_3$ is —OCH$_3$.

Another embodiment provides a compound of Formula (I) or a salt thereof, wherein $R_4$ is H.

Another embodiment provides a compound of Formula (I) or a salt thereof, wherein $R_4$ is —CH$_3$.

Another embodiment provides a compound of Formula (I) or a salt thereof, wherein $R_4$ is —OCH$_3$.

Another embodiment provides a compound of Formula (I) or a salt thereof, wherein R is —CH₃.

Another embodiment provides a compound of Formula (I) or a salt thereof, wherein R₅ is:

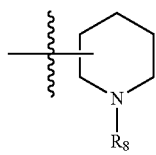

Another embodiment provides a compound of Formula (I) or a salt thereof, wherein R₅ is:

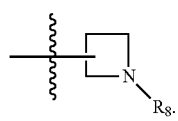

One embodiment provides a compound of Formula (I) or a salt thereof, wherein R₈ is H.

Another embodiment provides a compound of Formula (I) or a salt thereof, wherein R₈ is —CH₂C(CH₃)₂OH.

Another embodiment provides a compound of Formula (I) or a salt thereof, wherein R₈ is —C(O)CH₂N(CH₃)₂.

Another embodiment provides a compound of Formula (I) or a salt thereof, wherein R₈ is —CH₂CN.

Another embodiment provides a compound of Formula (I) or a salt thereof, wherein R₈ is —CH₂CH₂S(O)₂CH₃.

Another embodiment provides a compound of Formula (I) or a salt thereof, wherein R₈ is oxetanyl.

Another embodiment provides a compound of Formula (I) or a salt thereof, wherein R₈ is tetrahydropyranyl.

One embodiment provides a compound of Formula (I) or a salt thereof, wherein: R₁ is H;

R₂ is: —NHC(O)CH₃, or a cyclic group selected from:

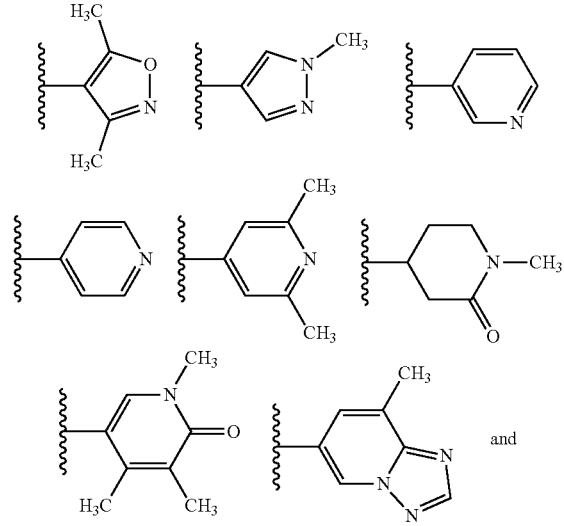

and

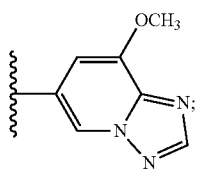

R₃ is H or —CH₃;
R₄ is H or —CH₃;
R₅ is:

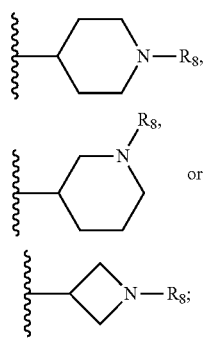

and

R₈ is hydrogen, —CH₂CN, —CH₂C(CH₃)₂OH, —C(O)CH₂N(CH₃)₂, —CH₂CH₂S(O)₂CH₃, oxetanyl, or tetrahydropyranyl.

Yet another embodiment provides at least one compound of Formula (I) or a salt thereof, wherein the compound is:

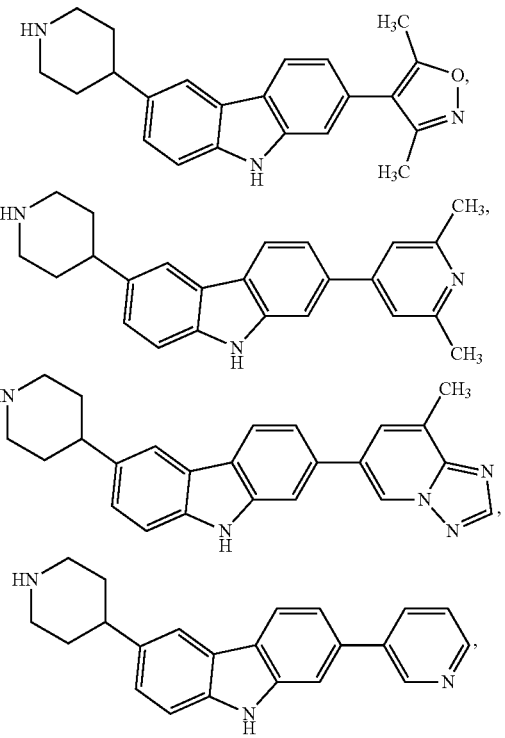

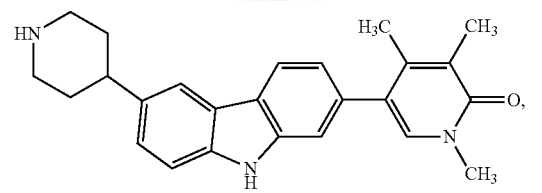
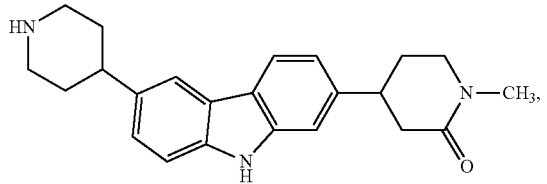
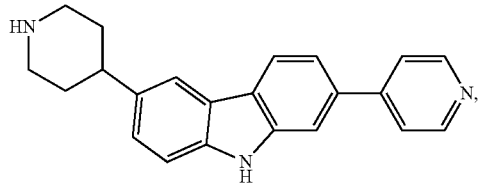
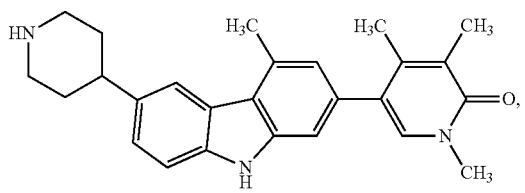
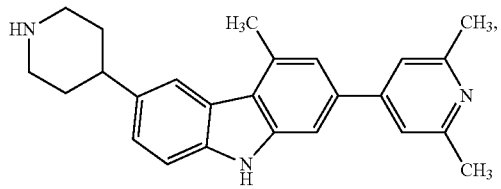
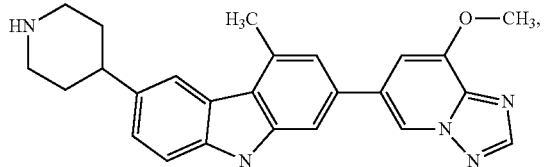
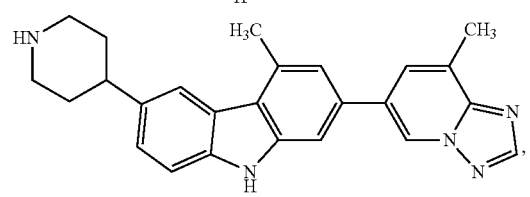
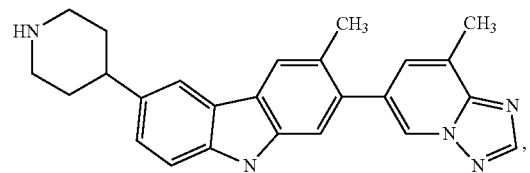
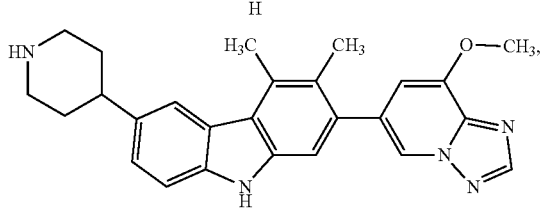
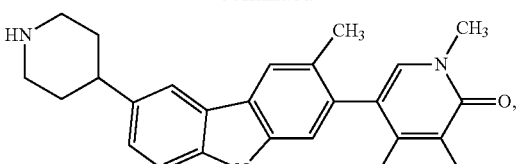
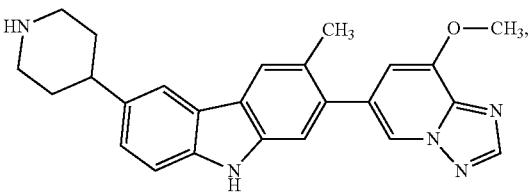
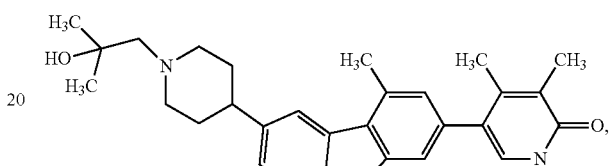
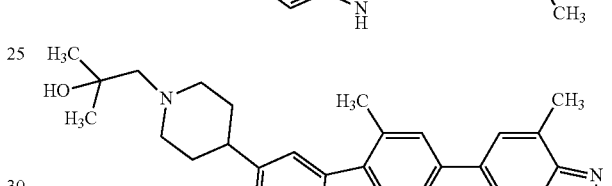
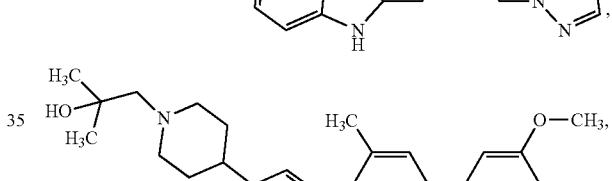
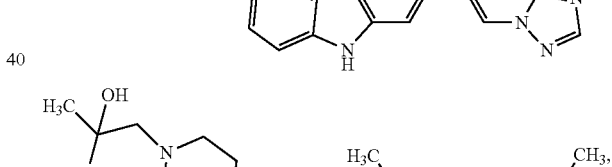
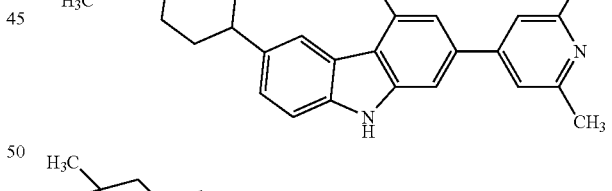
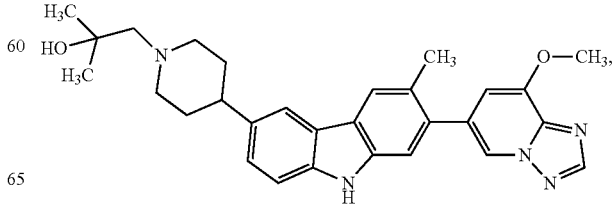

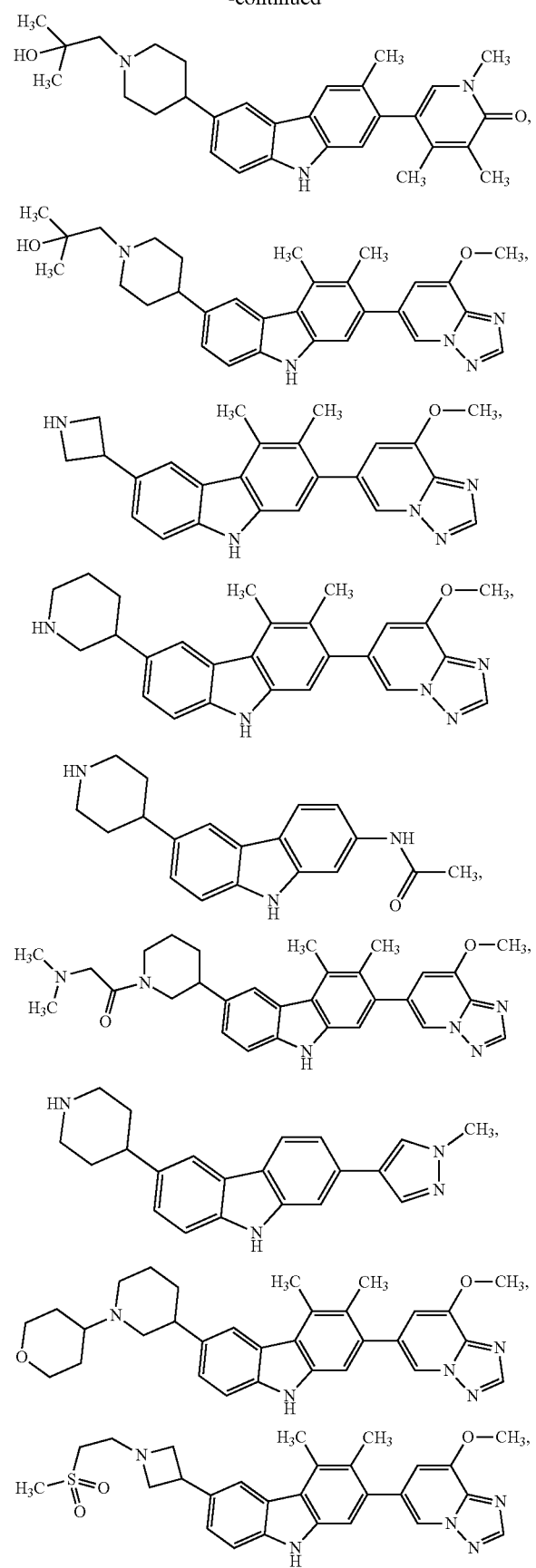
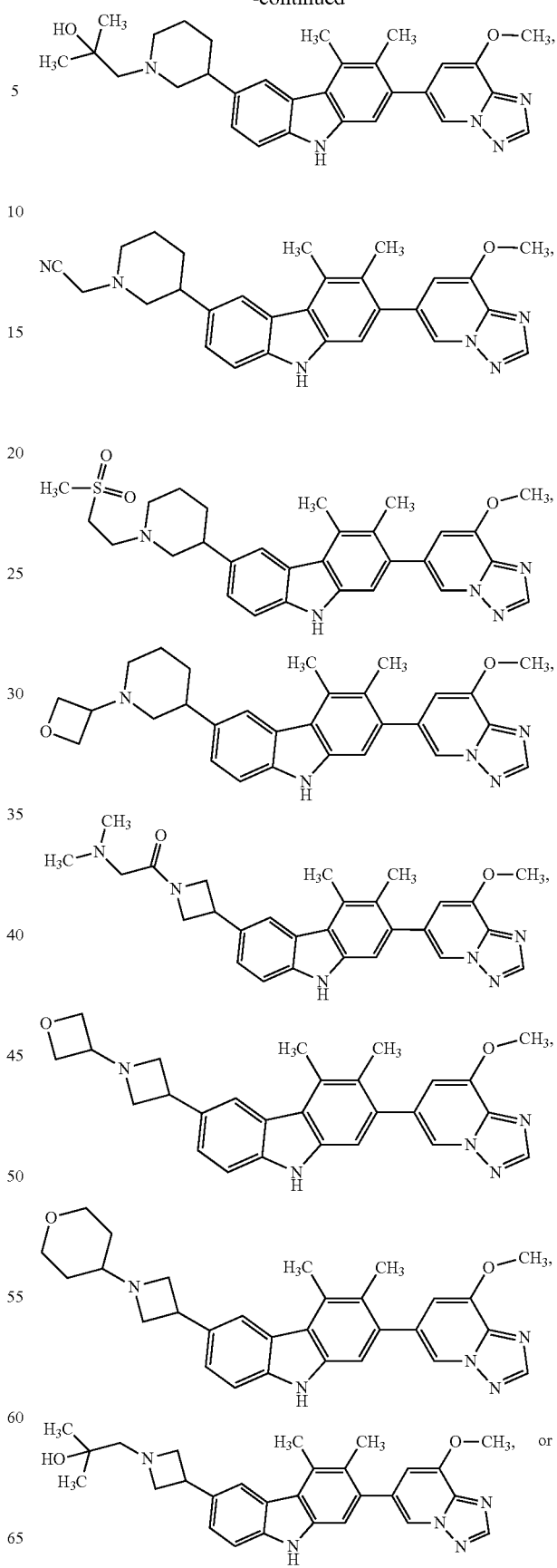

-continued

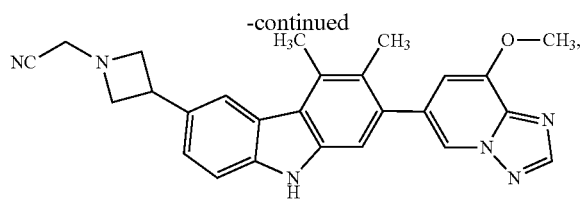

Another embodiment provides a pharmaceutical composition comprising a compound of Formula (I) or a salt thereof, and a pharmaceutically acceptable carrier.

In another embodiment, there is provided a compound of Formula (I) or a salt thereof, for use in therapy in treating autoimmune disease or chronic inflammatory disease.

Yet another embodiment provides a method for treating autoimmune disease or chronic inflammatory disease using a pharmaceutical composition comprising the compound of Formula (I) or a salt thereof. Also included in this embodiment are methods wherein said autoimmune disease or chronic inflammatory disease is selected from systemic lupus erythematosus (SLE), rheumatoid arthritis, multiple sclerosis (MS), and Sjögren's syndrome.

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. All references including patents, patent applications, and literature cited in the specification are expressly incorporated herein by reference in their entirety as if fully rewritten herein.

The features and advantages of the invention may be more readily understood by those of ordinary skill in the art upon reading the following detailed description. It is to be appreciated that certain features of the invention that are, for clarity reasons, described above and below in the context of separate embodiments, may be combined to form a single embodiment. Conversely, various features of the invention that are, for brevity reasons, described in the context of a single embodiment, may also be combined so as to form sub-combinations thereof.

Listed below are definitions of various terms used to describe the invention. The definitions set forth herein take precedence over definitions set forth in any patent, patent application, and/or publication incorporated herein by reference. These definitions apply to the terms as they are used throughout the specification (unless they are otherwise limited in specific instances) either individually or as part of a larger group.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight chain saturated aliphatic hydrocarbon groups containing, for example, from 1 to 3 carbon atoms. Examples of alkyl groups include, but are not limited to methyl (Me), ethyl (Et) and propyl (e.g., n-propyl and i-propyl). When numbers appear in a subscript after the symbol "C", the subscript defines with more specificity the number of carbon atoms that a particular group may contain. For example, "$C_{1-3}$ alkyl" denotes straight and branched chain alkyl groups with 1 to 3 carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids. It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are known in the art and are described in Rautio, J. et al., *Nature Review Drug Discovery*, 17, 559-587 (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a mixture, and formulation into an efficacious therapeutic agent. The present invention is intended to embody stable compounds.

"Therapeutically effective amount" is intended to include an amount of a compound of the present invention, alone or an amount of the combination of compounds claimed or an amount of a compound of the present invention in combination with other active ingredients, effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

The invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

UTILITY

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.)

according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil, or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. The following abbreviations are used:

ABBREVIATIONS

Ac acetyl
ACN acetonitrile
aq. aqueous
Bu butyl
CV column volumes
DCM dichloromethane
DMF dimethylformamide
DMSO dimethylsulfoxide
EtOAc ethyl acetate
Et ethyl
h, hr or hrs hour(s)
hex hexane
i iso
ISCO automated chromatography
HCl hydrochloric acid
HPLC high pressure liquid chromatography
LC liquid chromatography
M molar
mM millimolar
Me methyl
MeOH methanol
MHz megahertz
min. minute(s)
mins minute(s)
M+1 (M+H)$^+$
MS mass spectrometry
NBS N-bromosuccinimide
n or N normal
nm nanometer
nM nanomolar
Pd/C palladium on carbon
PdCl$_2$(dppf)$_2$ [1,1'-bis(diphenylphosphino)ferrocene]dichloropalladium(II)
Ph phenyl
PPh$_3$ triphenylphosphine
Pr propyl
psi pounds per square inch
rt room temperature
Ret Time retention time
sat. saturated
SFC supercritical fluid chromatography
TEA triethylamine
TFA trifluoroacetic acid
THF tetrahydrofuran
Preparations The preparations set out below are for the synthesis of reagents that were not obtained from commercial sources and were employed for the preparation of compounds of formula I of the invention. All chiral compounds in the Tables and Schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeters ("mm")). Gradient elution was performed with methanol/water mixtures in the presence of 0.1% trifluoroacetic acid.
HPLC Methods
Method A: (analytical) Column: Waters Acquity BEH® C18 2.0×50 mm, 1.7 μm (Waters Corp.); mobile phase A: water with 0.1% TFA; mobile phase B: MeCN with 0.1% TFA; temperature: 40° C.; flow rate 1 mL/min; gradient: 0-100% B over 1.5 min, then 0.5 min isocratic at 100% B.
Method B: (analytical) Column: Waters Acquity UPLC® BEH C18 2.1×50 mm, 1.7 μm (Waters Corp.); mobile phase A: water with 0.05% TFA; mobile phase B: MeCN with 0.05% TFA; temperature: 50° C.; flow rate 0.8 mL/min; gradient: 0-100% B over 1.8 min.
Method C: (analytical) Column: Waters Acquity UPLC® BEH C18 2.1×50 mm, 1.7 μm (Waters Corp.); mobile phase A: water with 0.1% TFA; mobile phase B: MeCN with 0.1% TFA; temperature: 50° C.; flow rate 1 mL/min; gradient: 0-100% B over 3 min, then 0.5 min isocratic at 100% B.
Method D: (QC-ACN-AA-XB) Column: Waters Acquity UPLC BEH® C18, 2.1×50 mm, 1.7-μm particles (Waters Corp.); mobile phase A: 5:95 acetonitrile:water with 10 mM ammonium acetate; mobile phase B: 95:5 acetonitrile:water with 10 mM ammonium acetate; temperature: 50° C.; gradient: 0-100% B over 3 minutes, then a 0.75-minute hold at 100% B; Flow: 1.0 mL/min; detection: UV at 220 nm.
Method E: (TS1) Column: Waters Acquity UPLC BEH® C18 (2.1×50 mm), 1.7 micron (Waters Corp.); solvent A=100% water with 0.05% TFA; solvent B=100% acetonitrile with 0.05% TFA; gradient=2-98% B over 1 minute, then a 0.5 minute hold at 98% B; Flow rate: 0.8 mL/min.
Method F: Column: Waters)(Bridge C18, 2.1 mm×50 mm, 1.7 μm particles (Waters Corp.); mobile Phase A: 5:95 acetonitrile:water with 0.1% trifluoroacetic acid; mobile Phase B: 95:5 acetonitrile:water with 0.1% trifluoroacetic acid; temperature: 50° C.; gradient: 0% B to 100% B over 3 min, then a 0.75 min hold at 100% B; flow: 1 mL/min; detection: MS and UV (220 nm).

Example 1

3,5-dimethyl-4-(6-(piperidin-4-yl)-9H-carbazol-2-yl) isoxazole

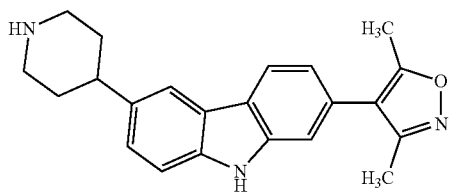
(1)

Step 1: Preparation of 4-(9H-carbazol-2-yl)-3,5-dimethylisoxazole

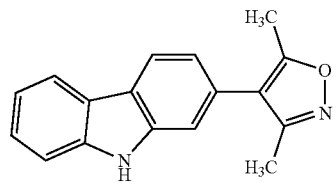
(1C)

To a mixture containing 2-bromo-9H-carbazole (750 mg, 3.05 mmol), 3,5-dimethyl-4-(4,4,5,5-tetramethyl-1,3,2-dioxaborolan-2-yl)isoxazole (748 mg, 3.35 mmol), and Pd(dppf)Cl₂ (55.7 mg, 0.076 mmol) in a screw cap vial was added THF (15 mL) followed by aqueous solution of potassium phosphate, tribasic (3.05 mL, 9.14 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 20 h. The reaction mixture was cooled to room temperature and diluted with EtOAc (15 mL). The aqueous layer thus obtained was aspirated using a Pasteur pipette, dried (Na₂SO₄), filtered and concentrated to obtain a crude product. The crude product was dissolved in a small amount of DCM and loaded on to a 24 g ISCO silica gel column and purified using the Teledyne ISCO system, eluting over a 15 min gradient with 0%-100% hexanes/ethyl acetate to obtain 4-(9H-carbazol-2-yl)-3,5-dimethylisoxazole (1C) (700 mg, 2.67 mmol, 88% yield), m/z (263, M+H).

Step 2: 4-(3,6-dibromo-9H-carbazol-2-yl)-3,5-dimethylisoxazole

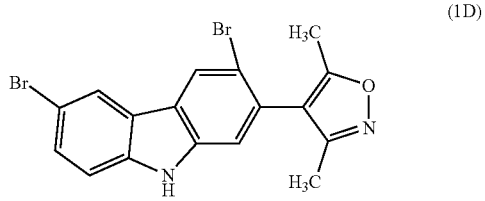 [SMILES: Cc1noc(C)c1-c1cc2[nH]c3ccc(Br)cc3c2cc1Br]
(1D)

To a solution containing 4-(9H-carbazol-2-yl)-3,5-dimethylisoxazole (500 mg, 1.906 mmol) in DMF (10 mL) was added NBS (700 mg, 4.0 mmol) in small portions. The reaction mixture was stirred for 20 h. A major di-brominated compound (m/z, 421, M+H) was detected. The reaction mixture was concentrated and the solids obtained were suspended in water and stirred. The solids were then filtered and dried, and the residue obtained was re-dissolved in DCM, adsorbed on to a silica gel (5 g) and purified on the ISCO silica gel chromatography system using a 24 g ISCO silica gel Column with Hex/EtOAc 0%-50% over a 15 min gradient to obtain 4-(3,6-dibromo-9H-carbazol-2-yl)-3,5-dimethylisoxazole (1D) (550 mg, ~90% purity), m/z (419/421, M+H).

Step 3: tert-butyl 4-(6-bromo-7-(3,5-dimethylisoxazol-4-yl)-9H-carbazol-3-yl)-5,6-dihydropyridine-1 (2H)-carboxylate

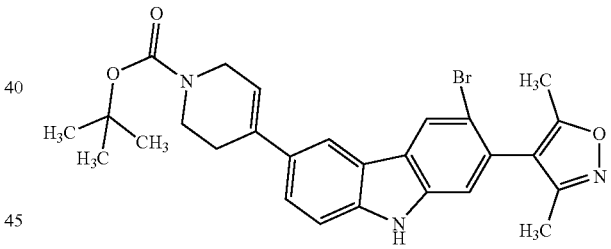
(1F)

To a mixture containing tert-butyl 4-(4,4,5,5-tetramethyl-1,3-dioxolan-2-yl)-5,6-dihydropyridine-1(2H)-carboxylate (122 mg, 0.393 mmol), 4-(3,6-dibromo-9H-carbazol-2-yl)-3,5-dimethylisoxazole (150 mg, 0.357 mmol), and Xphos-Pd G2 (7.02 mg, 8.93 µmol) in a screw cap vial was added THF (2 mL) followed by aqueous solution of potassium phosphate tribasic (0.357 mL, 1.071 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 40° C. for 20 h. The reaction mixture was cooled to room temperature, diluted with EtOAc (10 mL) and the aqueous layer was aspirated using a Pasteur pipette, dried (Na₂SO₄), filtered and concentrated to obtain a crude product. The crude product was dissolved in a small amount of DCM and charged to 12 g ISCO silica gel column and purified using the Teledyne ISCO system, eluting over a 15 min gradient with 0%-50% hexanes/ethyl acetate to obtain relatively clean tert-butyl 4-(6-bromo-7-(3,5-dimethylisoxazol-4-yl)-9H-carbazol-3-yl)-5,6-dihydropyridine-1(2H)-carboxylate (1F) (110 mg, 0.211 mmol, 59.0% yield, ~90% purity), m/z (524, M+H).

Steps 4 and 5

A solution containing impure tert-butyl 4-(6-bromo-7-(3,5-dimethylisoxazol-4-yl)-9H-carbazol-3-yl)-5,6-dihydropyridine-1(2H)-carboxylate (75 mg, 0.144 mmol) in MeOH (10 mL) in a Parr bottle, was purged with nitrogen gas. Next, Pd-C (76 mg, 0.072 mmol) was added. The vessel was fitted on a Parr hydrogen generator and pressurized to 50 psi with hydrogen gas. The reaction mixture was shaken for 20 h to obtain tert-butyl 4-(7-(3,5-dimethylisoxazol-4-yl)-9H-carbazol-3-yl)piperidine-1-carboxylate, m/z (446, M+H), along with other impurities. The reaction mixture was filtered through a pad of celite and concentrated. The crude material thus obtained was treated with TFA (2 mL) in DCM (2 mL) and stirred for 30 min. The reaction mixture was concentrated to dryness and the residue was purified via preparative LC/MS with the following conditions: Column: XBridge C18, 19×200 mm, 5-μm particles; mobile phase A: 5:95 acetonitrile: water with 10-mM ammonium acetate; mobile phase B: 95:5 acetonitrile:water with 10-mM ammonium acetate; gradient: 10-50% B over 19 minutes, then a 5-minute hold at 100% B; flow: 20 mL/min. Fractions containing the product were combined and dried via centrifugal evaporation to obtain 3,5-dimethyl-4-(6-(piperidin-4-yl)-9H-carbazol-2-30 yl)isoxazole (40 mg, 0.116 mmol, 81% yield), m/z (346, M+H). HPLC $t_R$ 1.2 min (analytical HPLC Method F). $^1$H NMR (500 MHz, DMSO-$d_6$) δ 11.27-11.23 (m, 1H), 8.20-8.15 (m, 1H), 7.98 (s, 1H), 7.48-7.41 (m, 2H), 7.32-7.27 (m, 1H), 7.15-7.10 (m, 1H), 3.79-3.55 (m, 2H), 3.26-3.19 (m, 1H), 2.92-2.78 (m, 2H), 2.45 (s, 3H), 2.29-2.25 (m, 3H), 1.93-1.86 (m, 2H), 1.86-1.74 (m, 2H).

Example 2

2-(2,6-Dimethylpyridin-4-yl)-6-(piperidin-4-yl)-9H-carbazole

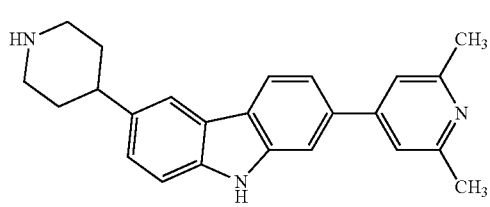
(2)

Step 1: 2-(4,4,5,5-tetramethyl-1,3,2-dioxaborolan-2-yl)-9H-carbazole

To a mixture containing 2-bromo-9H-carbazole (1 g, 4.06 mmol), 4,4,4',4',5,5,5',5'-octamethyl-2,2'-bi(1,3,2-dioxaborolane) (1.548 g, 6.10 mmol), potassium acetate (1.196 g, 12.19 mmol) and Pd(dppf)Cl$_2$ (0.149 g, 0.203 mmol) in a screw cap vial was added DMF (15 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 85° C. for 4 h. The reaction mixture was cooled to room temperature, diluted with EtOAc (100 mL) and washed with 10% LiCl aq. solution (25 mL×2) and sat. aq. NaCl solution (25 mL), dried (Na$_2$SO$_4$), filtered and concentrated to obtain a crude residue. The crude residue was re-dissolved in DCM (20 mL), adsorbed on to silica gel (15 g) and purified on the ISCO silica gel chromatography system using a 40 g ISCO silica gel column with Hex/EtOAc (0%-50%) over a 15 min gradient to obtain 2-(4,4,5,5-tetramethyl-1,3,2-dioxaborolan-2-yl)-9H-carbazole (2A) (1.1 g, 3.75 mmol, 92% yield), m/z (294, M+H).

Step 2: 2-(2,6-dimethylpyridin-4-yl)-9H-carbazole

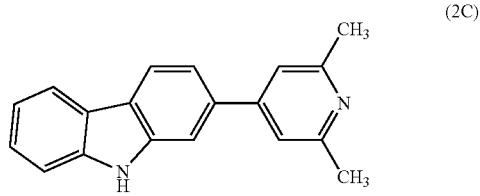 [SMILES: Cc1cc(-c2ccc3c(c2)[nH]c2ccccc23)cc(C)n1]
(2C)

To a mixture containing 2-(4,4,5,5-tetramethyl-1,3,2-dioxaborolan-2-yl)-9H-carbazole (200 mg, 0.682 mmol), 4-bromo-2,6-dimethylpyridine (133 mg, 0.716 mmol), and Pd(dppf)Cl$_2$ (12.48 mg, 0.017 mmol) in a screw cap vial was added THF (5 mL) followed by aqueous solution of potassium phosphate tribasic (0.682 mL, 2.047 mmol).

The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 20 h. The reaction mixture was cooled to room temperature, diluted with EtOAc (15 mL) and the aqueous layer was aspirated using a Pasteur pipette, dried (Na$_2$SO$_4$), filtered and concentrated to obtain crude product. The crude product was dissolved in a small amount of DCM and charged on to 24 g ISCO silica gel column and purified using the Teledyne ISCO system, eluting over a 15 min gradient with 5%-100% hexane/ethyl acetate to obtain 2-(2,6-dimethylpyridin-4-yl)-9H-carbazole (2C) (130 mg, 0.477 mmol, 70.0% yield), m/z (273, M+H).

Step 3:
6-bromo-2-(2,6-dimethylpyridin-4-yl)-9H-carbazole

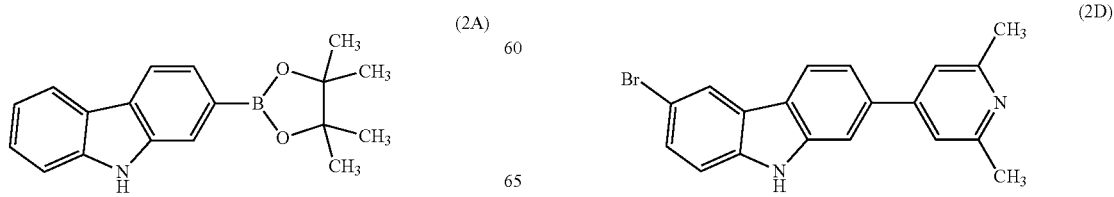

To a solution of 2-(2,6-dimethylpyridin-4-yl)-9H-carbazole (100 mg, 0.367 mmol) in DCM was added NBS (65.4 mg, 0.367 mmol) in small portions. The reaction mixture was stirred for 20 h. LCMS analysis displayed 6-bromo-2-(2,6-dimethylpyridin-4-yl)-9H-carbazole, along with minor brominated isomers. To the reaction mixture was added silica gel (5 g) and additional DCM, and the contents were concentrated to dryness. The silica adsorbed material was purified on 12 g ISCO silica gel column and purified using the Teledyne ISCO system, eluting over a 15 min gradient with CH$_2$Cl$_2$/EtOAc (0%-50%) over a 15 min gradient to obtain 6-bromo-2-(2,6-dimethylpyridin-4-yl)-9H-carbazole (2D) (75 mg), m/z (351/353, M+H), along with minor brominated isomers.

Steps 4 to 6

To a mixture containing crude 6-bromo-2-(2,6-dimethylpyridin-4-yl)-9H-carbazole (75 mg, 0.214 mmol), tert-butyl 4-(4,4,5,5-tetramethyl-1,3,2-dioxaborolan-2-yl)-5,6-dihydropyridine-1(2H)-carboxylate (72.6 mg, 0.235 mmol), and Pd(dppf)Cl$_2$ (7.81 mg, 10.68 µmol) in a screw cap vial was added THF (2.5 mL) followed by aqueous solution of potassium phosphate tribasic (0.214 mL, 0.641 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 20 h. The reaction mixture was cooled to room temperature, diluted with EtOAc (10 mL) and the bottom aqueous layer was aspirated using a pipette. The organic layer was dried (Na$_2$SO$_4$), filtered and concentrated to obtain a crude product. The crude product was dissolved in a small amount of DCM and charged on to 12 g ISCO silica gel column and purified using the Teledyne ISCO system, eluting over a 10 min gradient with 0%-100% hexanes/ethyl acetate to obtain crude tert-butyl 4-(7-(2,6-dimethylpyridin-4-yl)-9H-carbazol-3-yl)-5,6-dihydropyridine-1(2H)-carboxylate, m/z (454, M+H).

Tert-butyl 4-(7-(2,6-dimethylpyridin-4-yl)-9H-carbazol-3-yl)-5,6-dihydropyridine-1(2H)-carboxylate was dissolved in methanol (5 mL) and transferred to a Parr bottle. The vessel was purged with nitrogen gas and 10% Pd-C (50 mg, 0.047 mmol) was added. The vessel was fitted to a Parr Shaker, pressurized with hydrogen gas at 50 psi and shaken for 20 h. The reaction mixture was filtered through a plug of celite and concentrated to obtain crude tert-butyl 4-(7-(2,6-dimethylpyridin-4-yl)-9H-carbazol-3-yl)piperidine-1-carboxylate, m/z (456, M+H).

Tert-butyl 4-(7-(2,6-dimethylpyridin-4-yl)-9H-carbazol-3-yl)piperidine-1-carboxylate was dissolved in DCM (1 mL) and treated with TFA (1 mL). The reaction mixture was stirred for 1 h to facilitate the removal of the tert-butylcarboxy group. The reaction mixture was concentrated and purified using preparative LC/MS with the following conditions: Column:)(Bridge C18, 19×200 mm, 5-µm particles; mobile phase A: 5:95 acetonitrile:water with 0.1% trifluoroacetic acid; mobile phase B: 95:5 acetonitrile:water with 0.1% trifluoroacetic acid; gradient: 0-30% B over 24 minutes, then a 5-minute hold at 100% B; flow: 20 mL/min. Fractions containing the product were combined and dried via centrifugal evaporation to obtain 2-(2,6-dimethylpyridin-4-yl)-6-(piperidin-4-yl)-9H-carbazole (3.9 mg, 10.97 µmol, 5.14% yield), m/z (356, M+H). HPLC t$_R$ 0.77 min (analytical HPLC Method F). $^1$H NMR (500 MHz, DMSO-d$_6$) δ 11.47 (s, 1H), 8.29-8.25 (m, 1H), 8.05-8.02 (m, 1H), 7.99-7.96 (m, 1H), 7.88-7.84 (m, 2H), 7.70-7.65 (m, 1H), 7.54-7.51 (m, 1H), 7.38-7.34 (m, 1H), 3.46-3.40 (m, 1H), 3.12-2.98 (m, 4H), 2.66-2.62 (m, 6H), 2.09-2.02 (m, 2H), 1.97-1.86 (m, 2H)

Example 3

2-(8-methyl-[1,2,4]triazolo[1,5-a]pyridin-6-yl)-6-(piperidin-4-yl)-9H-carbazole

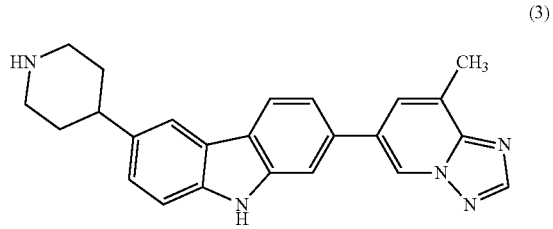 [SMILES: Cc1cc(-c2ccc3c(c2)[nH]c2ccc(C4CCNCC4)cc23)cn2ncnc12]

(3)

Step 1: 2-(8-methyl-[1,2,4]triazolo[1,5-a]pyridin-6-yl)-9H-carbazole

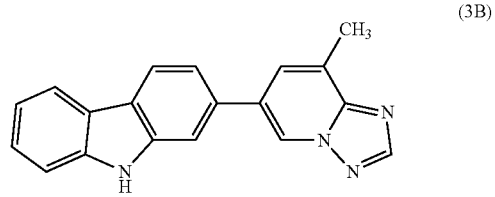 [SMILES: Cc1cc(-c2ccc3c(c2)[nH]c2ccccc23)cn2ncnc12]

(3B)

To a mixture containing 2-(4,4,5,5-tetramethyl-1,3,2-dioxaborolan-2-yl)-9H-carbazole (200 mg, 0.682 mmol), 6-bromo-8-methyl-[1,2,4]triazolo[1,5-a]pyridine (145 mg, 0.682 mmol), and Pd(dppf)Cl$_2$ (12.48 mg, 0.017 mmol) in a screw cap vial was added THF (5 mL) followed by aqueous solution of potassium phosphate, tribasic (0.682 mL, 2.047 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 20 h. The reaction mixture was cooled to room temperature, diluted with EtOAc (10 mL) and the aqueous layer was removed using a Pasteur pipette and organic layer concentrated. The crude product was dissolved in a small amount of DCM and charged to 12 g ISCO silica gel column and purified using the Teledyne ISCO system, eluting over a 15 min gradient with 0%-100% hexanes/ethyl acetate to obtain crude 2-(8-methyl-[1,2,4]triazolo[1,5-a]pyridin-6-yl)-9H-carbazole (3B) (150 mg), m/z (299, M+H), contaminated with 6-bromo-8-methyl-[1,2,4]triazolo[1,5-a]pyridine.

Step 2: 3,6-dibromo-2-(8-methyl-[1,2,4]triazolo[1,5-a]pyridin-6-yl)-9H-carbazole

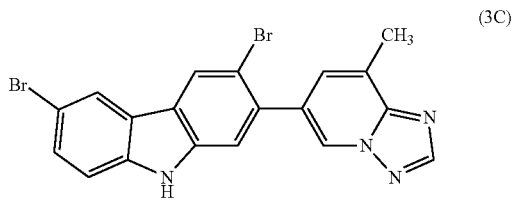 [SMILES: Cc1cc(-c2cc3[nH]c4ccc(Br)cc4c3cc2Br)cn2ncnc12]

(3C)

To a solution containing 2-(8-methyl-[1,2,4]triazolo[1,5-a]pyridin-6-yl)-9H-carbazole (100 mg, 0.335 mmol) in DCM (5 mL) was added NBS (119 mg, 0.670 mmol) and the reaction mixture was stirred overnight. The reaction mixture was diluted with additional DCM (5 mL) and dry silica gel (5 g) was added, and concentrated to dryness. The silica adsorbed material was purified on 12 g ISCO silica gel column and purified using the Teledyne ISCO system, eluting over a 15 min gradient with $CH_2Cl_2$/EtOAc (0%-50%) over a 15 min gradient to obtain crude 3,6-dibromo-2-(8-methyl-[1,2,4]triazolo[1,5-a]pyridin-6-yl)-9H-carbazole (3C) (150 mg), m/z (457, m+H).

Steps 3 and 4: tert-butyl 4-(7-(8-methyl-[1,2,4]triazolo[1,5-a]pyridin-6-yl)-9H-carbazol-3-yl)piperidine-1-carboxylate

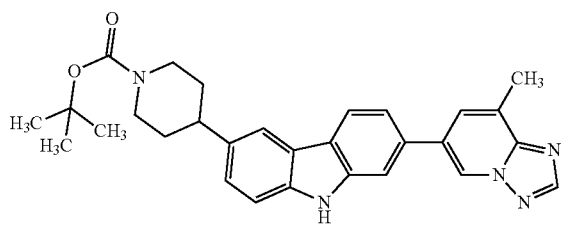

(3D)

To a mixture containing 3,6-dibromo-2-(8-methyl-[1,2,4]triazolo[1,5-a]pyridin-6-yl)-9H-carbazole (150 mg, 0.329 mmol), tert-butyl 4-(4,4,5,5-tetramethyl-1,3,2-dioxaborolan-2-yl)-5,6-dihydropyridine-1(2H)-carboxylate (112 mg, 0.362 mmol), and Pd(dppf)$Cl_2$ (12.03 mg, 0.016 mmol) in a screw cap vial was added THF (2.5 mL) followed by aqueous solution of potassium phosphate, tribasic (0.329 mL, 0.987 mmol). The vial was fitted with a Teflon lined septum cap. The system was evacuated under vacuum (via a needle from a nitrogen/vacuum manifold line) and back-filled with nitrogen gas. The procedure was repeated three times. The needle was removed and the vial was heated at 55° C. for 20 h. The reaction mixture was cooled to room temperature, diluted with EtOAc (10 mL) and the bottom aqueous layer was aspirated out using a pipette. The organic layer was dried ($Na_2SO_4$), filtered and concentrated to obtain crude product. The crude product was dissolved in a small amount of DCM and charged to 12 g ISCO silica gel column and purified using the Teledyne ISCO system, eluting over a 10 min gradient with 0%-100% hexanes/ethyl acetate to obtain impure tert-butyl 4-(6-bromo-7-(8-methyl-[1,2,4]triazolo[1,5-a]pyridin-6-yl)-9H-carbazol-3-yl)-5,6-dihydropyridine-1(2H)-carboxylate, m/z (557/559, M+H). The crude product was suspended in MeOH (2.5 mL) and Pd(OH)$_2$ (10 mg, 0.071 mmol) was added followed by the addition of ammonium formate (150 mg, 2.379 mmol). The reaction mixture vial was sealed and heated at 55° C. for 20 h. The reaction mixture was diluted with ethyl acetate (5 mL), filtered through a plug of celite and concentrated. The crude material was purified using prep HPLC (Solvent A: 95% $H_2O$/5% ACN/0.05% TFA, column: 2-Phen Luna C18 (21×100) to obtain pure tert-butyl 4-(7-(8-methyl-[1,2,4]triazolo[1,5-a]pyridin-6-yl)-9H-carbazol-3-yl)piperidine-1-carboxylate (3D) (30 mg, 0.062 mmol, 18.94% yield), m/z (482, M+H).

Step 5

To a solution containing tert-butyl 4-(7-(8-methyl-[1,2,4]triazolo[1,5-a]pyridin-6-yl)-9H-carbazol-3-yl)piperidine-1-carboxylate (30 mg, 0.062 mmol) in DCM (1 mL) was added TFA (1 ml, 12.98 mmol). The reaction mixture was stirred for 30 min and concentrated. The residue was suspended in diethyl ether (1 mL), sonicated till a fine suspension was formed. The suspension was filtered, rinsed with additional diethylether and dried to obtain 2-(8-methyl-[1,2,4]triazolo[1,5-a]pyridin-6-yl)-6-(piperidin-4-yl)-9H-carbazole, TFA (25 mg, 0.045 mmol, 72.9% yield) as a solid, m/z (382, M+H).). HPLC $t_R$ 0.7 min (analytical HPLC Method E). $^1$H NMR (400 MHz, $CD_3OD$_SPE) δ 8.73-8.71 (m, 1H), 8.54-8.51 (m, 1H), 8.16-8.11 (m, 2H), 7.61-7.58 (m, 1H), 7.52-7.40 (m, 3H), 7.27-7.20 (m, 1H), 3.50-3.43 (m, 2H), 3.13-2.94 (m, 3H), 2.74-2.71 (m, 3H), 2.20-2.08 (m, 4H).

Example 4

6-(piperidin-4-yl)-2-(pyridin-3-yl)-9H-carbazole

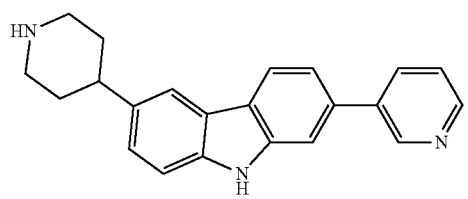

(4)

6-(Piperidin-4-yl)-2-(pyridin-3-yl)-9H-carbazole was prepared in according to the general process described in Example 1, starting with 2-bromo-9H-carbazole and 3-(4,4,5,5-tetramethyl-1,3,2-dioxaborolan-2-yl)pyridine to afford 6-(piperidin-4-yl)-2-(pyridin-3-yl)-9H-carbazole, 2 TFA, m/z (328, M+H). HPLC $t_R$ 0.7 min (analytical PLC Method F). $^1$H NMR (400 MHz, DMSO-$d_6$) δ 11.43-11.39 (m, 1H), 9.09 (br s, 1H), 8.71-8.65 (m, 1H), 8.39 (br d, J=7.8 Hz, 1H), 8.26 (d, J=8.2 Hz, 1H), 8.01 (s, 1H), 7.82 (s, 1H), 7.73-7.66 (m, 1H), 7.58-7.53 (m, 1H), 7.52-7.48 (m, 1H), 7.33-7.30 (m, 1H), 3.47-3.41 (m, 2H), 3.15-2.96 (m, 3H), 2.10-2.02 (m, 2H), 1.99-1.85 (m, 2H).

Example 5

1,3,4-trimethyl-5-(6-(piperidin-4-yl)-9H-carbazol-2-yl)pyridin-2(1H)-one

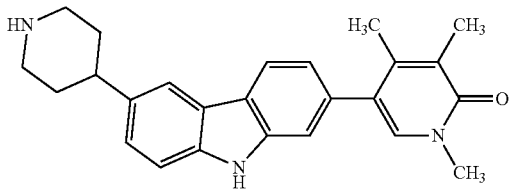

(5)

Step 1: 4'-bromo-5-chloro-2-nitro-1,1'-biphenyl

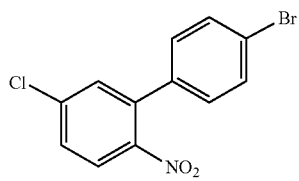

(5C)

To a mixture containing 2-bromo-4-chloro-1-nitrobenzene (1500 mg, 6.34 mmol), (4-bromophenyl)boronic acid (1299 mg, 6.47 mmol), and Pd(dppf)Cl$_2$ (116 mg, 0.159 mmol) in a screw cap vial was added THF (15 mL) followed by aqueous solution of potassium phosphate, tribasic (6.34 mL, 19.03 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 20 h. The reaction mixture was cooled to room temperature, diluted with EtOAc (50 mL) and the bottom aqueous layer was discarded and the organic layer was dried (Na$_2$SO$_4$), filtered and concentrated to obtain crude product. The crude product was dissolved in a small amount of DCM and charged on to 40 g ISCO silica gel column and purified using the Teledyne ISCO system, eluting over a 20 min gradient with 0%-50% hexanes/ethyl acetate to obtain 4'-bromo-5-chloro-2-nitro-1,1'-biphenyl (5C) (1850 mg, 5.92 mmol, 93% yield), m/z not detected. $^1$H NMR (400 MHz, DMSO-d$_6$) δ 8.11-8.07 (m, 1H), 7.77-7.72 (m, 1H), 7.71-7.65 (m, 3H), 7.38-7.33 (m, 2H).

Step 2: 2-bromo-6-chloro-9H-carbazole

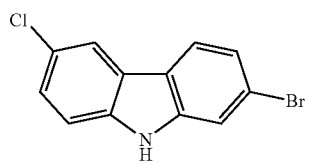

(5D)

A mixture containing 4'-bromo-5-chloro-2-nitro-1,1'-biphenyl (1900 mg, 6.08 mmol) and triphenylphosphine (4000 mg, 15.25 mmol) was suspended in o-dichlorobenzene (20 mL) in a high pressure vessel, sealed and pump-purged with nitrogen gas and heated at 185° C. for 20 h. The reaction mixture was cooled to room temperature and concentrated. The residue was dissolved in DCM and adsorbed to silica gel (~20 g) and dry loaded into an Teledyne ISCO empty cartridge and fitted on an ISCO Teledyne system and purified using a 80 g ISCO silica gel column with Hex/EtOAc (0%-50%) over a 20 min gradient to obtain 2-bromo-6-chloro-9H-carbazole (5D) (1500 mg, 5.35 mmol, 88% yield), m/z (280, M+H).

Step 3: 6-chloro-2-(4,4,5,5-tetramethyl-1,3,2-dioxaborolan-2-yl)-9H-carbazole

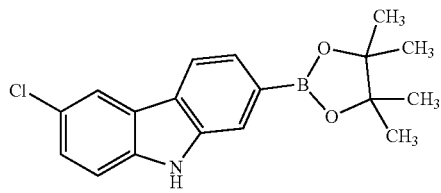

(5E)

To a mixture containing 2-bromo-6-chloro-9H-carbazole (500 mg, 1.782 mmol), 4,4,4',4',5,5,5',5'-octamethyl-2,2'-bi(1,3,2-dioxaborolane) (566 mg, 2.228 mmol), and potassium acetate (525 mg, 5.35 mmol) in a screw cap vial was added DMF (10 mL).

The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 85° C. for 20 h. The reaction mixture was cooled to room temperature, diluted with EtOAc (100 mL), transferred to a separating funnel and washed with aq. 10% LiCl solution (2×30 mL) and sat. aq. NaCl solution (1×30 mL). The organic layer was dried (Na$_2$SO$_4$), filtered and concentrated to obtain crude product. The crude product was dissolved in a small amount of DCM and charged to 24 g ISCO silica gel Column and purified using the Teledyne ISCO system, eluting over a 15 min gradient with 0%-50% hexanes/ethyl acetate to obtain 6-chloro-2-(4,4,5,5-tetramethyl-1,3,2-dioxaborolan-2-yl)-9H-carbazole (5E) (510 mg, 1.557 mmol, 87% yield), m/z (328, M+H).

Steps 4 and 5: tert-butyl 4-(7-(1,4,5-trimethyl-6-oxo-1,6-dihydropyridin-3-yl)-9H-carbazol-3-yl)-5,6-dihydropyridine-1(2H)-carboxylate

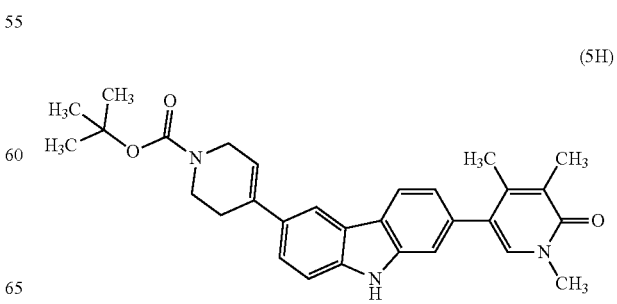

(5H)

To a mixture containing 6-chloro-2-(4,4,5,5-tetramethyl-1,3,2-dioxaborolan-2-yl)-9H-carbazole (50 mg, 0.153 mmol), 5-bromo-1,3,4-trimethylpyridin-2(1H)-one (33.0 mg, 0.153 mmol), and Xphos Pd G2 (3.00 mg, 3.82 µmol) in a screw cap vial was added THF (1 mL) followed by aqueous solution of 3N potassium phosphate, tribasic (0.305 mL, 0.916 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 4 h. The reaction mixture was cooled to room temperature, and tert-butyl 4-(4,4,5,5-tetramethyl-1,3,2-dioxaborolan-2-yl)-5,6-dihydropyridine-1(2H)-carboxylate (59.0 mg, 0.191 mmol) and Xphos Pd G2 (3.00 mg, 3.82 µmol) were added in one portion. The vial was re-sealed with a Teflon lined septum cap. The system was subjected to the same evacuation/backfill protocol with nitrogen gas as above (3 X). The needle was removed and the vial was heated at 75° C. for additional 6 h. The reaction mixture was cooled to room temperature and diluted with ethyl acetate (5 mL) and water (1 mL). The bottom aqueous layer was aspirated out using a pipette. The organic layer was dried (Na$_2$SO$_4$), filtered and concentrated. The crude product was dissolved in a small amount of DCM and charged to 4 g ISCO silica gel column and purified using the Teledyne ISCO system, eluting over a 10 min gradient with 20%-100% hexanes/ethyl acetate to obtain tert-butyl 4-(7-(1,4,5-trimethyl-6-oxo-1,6-dihydropyridin-3-yl)-9H-carbazol-3-yl)-5,6-dihydropyridine-1(2H)-carboxylate (5H) (60 mg, 80%), m/z (484, M+H).

Steps 6 and 7

To a solution containing tert-butyl 4-(7-(1,4,5-trimethyl-6-oxo-1,6-dihydropyridin-3-yl)-9H-carbazol-3-yl)-5,6-dihydropyridine-1(2H)-carboxylate (50 mg, 0.103 mmol) in MeOH (5 mL) was added 10% Pd-C (27.5 mg, 0.026 mmol) followed by ammonium formate (130 mg, 2.068 mmol). The vial was sealed and heated at 40° C. for 4 h. The reaction mixture was filtered through a pad of celite and pad rinsed with additional methanol (~5 mL). The filtrate was concentrated, re-dissolved in ethyl acetate (20 mL) and washed with water (2×5 mL), and sat. aq. NaCl solution (1×5), dried (Na$_2$SO$_4$), filtered and concentrated to obtain tert-butyl 4-(7-(1,4,5-trimethyl-6-oxo-1,6-dihydropyridin-3-yl)-9H-carbazol-3-yl)piperidine-1-carboxylate. The residue was dissolved in DCM (2 mL) and treated with TFA (1 mL). The reaction mixture was stirred for 1 h, concentrated and the crude product subjected to HPLC purification. The crude material was purified via preparative LC/MS with the following conditions: Column: XBridge C18 (19×200 mm), 5-µm particles; mobile phase A: 5:95 acetonitrile:water with 10-mM ammonium acetate; mobile phase B: 95:5 acetonitrile:water with 10-mM ammonium acetate; gradient: 5-60% B over 20 minutes, then a 4-minute hold at 100% B; Flow: 20 mL/min. Fractions containing the product were combined and dried via centrifugal evaporation to obtain 1,3,4-trimethyl-5-(6-(piperidin-4-yl)-9H-carbazol-2-yl)pyridin-2(1H)-one (38 mg, 0.098 mmol, 94% yield), m/z (386, M+H). HPLC t$_R$ 1.0 min (analytical HPLC Method F). $^1$H NMR (500 MHz, DMSO-d$_6$) δ 11.21-11.16 (m, 1H), 8.12-8.08 (m, 1H), 7.99-7.95 (m, 1H), 7.53-7.49 (m, 1H), 7.45 (d, J=8.2 Hz, 1H), 7.36-7.32 (m, 1H), 7.31-7.27 (m, 1H), 7.04 (br d, J=7.9 Hz, 1H), 3.49 (4, 3H), 3.36-3.30 (m, 2H), 3.00-2.90 (m, 3H), 2.07 (s, 3H), 2.06 (s, 3H), 2.00-1.94 (m, 2H), 1.93-1.81 (m, 2H).

Example 6

1-methyl-4-(6-(piperidin-4-yl)-9H-carbazol-2-yl)piperidin-2-one

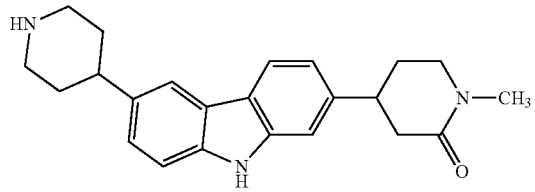

(6)

Steps 1 and 2: tert-butyl 4-(7-(1-methyl-2-oxo-1,2-dihydropyridin-4-yl)-9H-carbazol-3-yl)-5,6-dihydropyridine-1(2H)-carboxylate

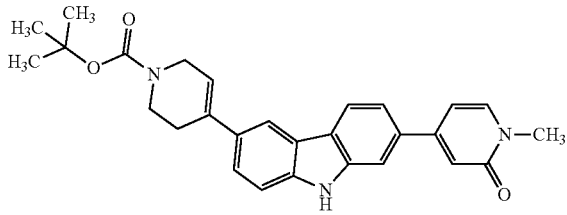

(6B)

To a mixture containing 6-chloro-2-(4,4,5,5-tetramethyl-1,3,2-dioxaborolan-2-yl)-9H-carbazole (35 mg, 0.107 mmol), 4-bromo-1-methylpyridin-2(1H)-one (20.09 mg, 0.107 mmol) and Xphos Pd G2 (2.101 mg, 2.67 µmol) in a screw cap vial was added THF (1 mL) followed by aqueous solution of potassium phosphate, tribasic (0.215 mL, 0.650 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 4 h. The reaction mixture was cooled to room temperature and tert-butyl 4-(4,4,5,5-tetramethyl-1,3,2-dioxaborolan-2-yl)-5,6-dihydropyridine-1(2H)-carboxylate (40 mg, 0.130 mmol) and Xphos Pd G2 (2.00 mg, 2.67 µmol) were added. The vial was re-sealed with a Teflon lined septum cap. The system was subjected to the same evacuation/backfill protocol with nitrogen gas as described above (3 times). The needle was removed and the vial was heated at 75° C. for additional 6 h. The reaction mixture was cooled to room temperature and diluted with ethyl acetate (5 mL) and water (1 mL) and the bottom aqueous layer was aspirated using a pipette. The organic layer was dried (Na$_2$SO$_4$), filtered and concentrated. The crude product was dissolved in a small amount of DCM and charged to 4 g ISCO silica gel column and purified using the Teledyne ISCO system, eluting over a 10 min gradient with 20%-100% hexanes/ethyl acetate to obtain tert-butyl 4-(7-(1-methyl-2-oxo-1,2-dihydropyridin-4-yl)-9H-carbazol-3-yl)-5,6-dihydropyridine-1(2H)-carboxylate (6B) (36 mg, 0.079 mmol, 74.0% yield) m/z (456, M+H).

Steps 3 and 4: 1-methyl-4-(6-(piperidin-4-yl)-9H-carbazol-2-yl)piperidin-2-one

To a solution containing tert-butyl 4-(7-(1-methyl-2-oxo-1,2-dihydropyridin-4-yl)-9H-carbazol-3-yl)-5,6-dihydro-pyridine-1(2H)-carboxylate (50 mg, 0.110 mmol) in MeOH (5 mL) was added 10% Pd-C (29.2 mg, 0.027 mmol) followed by ammonium formate (150 mg, 2.068 mmol). The vial was sealed and heated at 40° C. for 6 h. The reaction mixture was filtered through a pad of celite and the pad was rinsed with additional methanol. The filtrate was concentrated, dissolved in ethyl acetate (20 mL) and washed with water (2×2 mL), and sat. aq. NaCl solution (1×2 mL), dried ($Na_2SO_4$), filtered and concentrated. The residue was dissolved in DCM (2 mL) and treated with TFA (1 mL) and the reaction mixture stirred for 1 h. The reaction mixture was concentrated and the crude product was subjected to HPLC purification. The crude material was purified via preparative LC/MS with the following conditions: Column: XBridge C18, 19×200 mm, 5-μm particles; mobile phase A: 5:95 acetonitrile:water with 10-mM ammonium acetate; mobile phase B: 95:5 acetonitrile:water with 10-mM ammonium acetate; gradient: 10-60% B over 19 minutes, then a 5-minute hold at 100% B; Flow: 20 mL/min. Fractions containing the product were combined and dried via centrifugal evaporation to obtain 1-methyl-4-(6-(piperidin-4-yl)-9H-carbazol-2-yl)piperidin-2-one (25 mg, 0.069 mmol, 63.0% yield), m/z (362, M+H). HPLC $t_R$ 0.90 min (analytical HPLC Method F). $^1$H NMR (500 MHz, DMSO-$d_6$) δ 11.06-11.03 (s, 1H), 8.03-7.97 (m, 1H), 7.93-7.88 (m, 1H), 7.40 (br d, J=8.2 Hz, 1H), 7.32 (s, 1H), 7.27-7.23 (m, 1H), 7.06 (br d, J=7.9 Hz, 1H), 3.85-3.74 (m, 2H), 3.46-3.38 (m, 1H), 3.34-3.16 (m, 4H), 2.94-2.83 (m, 5H), 2.48-2.38 (m, 1H), 2.10-1.76 (m, 6H).

Example 7

N-(6-(piperidin-4-yl)-9H-carbazol-2-yl)acetamide

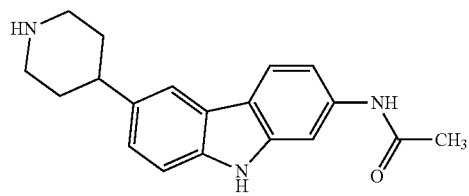

(7)

Step 1: N-(6-chloro-9H-carbazol-2-yl)acetamide

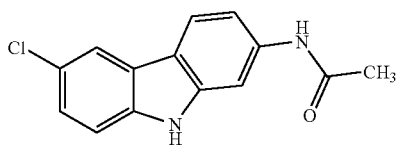

(7A)

To a mixture containing 2-bromo-6-chloro-9H-carbazole (25 mg, 0.089 mmol), di-tert-butyl(2', 4', 6'-triisopropyl-3,4,5,6-tetramethyl-[1,1'-biphenyl]-2-yl)phosphine (2.57 mg, 5.35 acetamide (10.53 mg, 0.178 mmol), potassium phosphate, tribasic (28.4 mg, 0.134 mmol) and tris(dibenzylideneacetone)dipalladium(0) (1 mg, 1.092 μmol) in a screw cap vial was added t-butanol (1 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 100° C. for 20 h. The reaction mixture was cooled to room temperature and concentrated. The residue was suspended in water (1 mL) and filtered and dried to obtain N-(6-chloro-9H-carbazol-2-yl)acetamide (7A) (13 mg, 0.050 mmol, 56%), m/z (259, M+H).

Step 2: tert-butyl 4-(7-acetamido-9H-carbazol-3-yl)piperidine-1-carboxylate

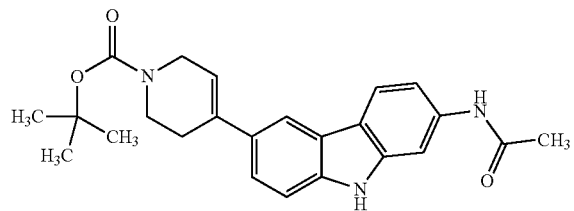

(7B)

To a mixture containing N-(6-chloro-9H-carbazol-2-yl)acetamide (15 mg, 0.05 mmol), Xphos Pd G2 (1.753 mg, 2.228 μmol), and tert-butyl 4-(4,4,5,5-tetramethyl-1,3,2-dioxaborolan-2-yl)-5,6-dihydropyridine-1(2H)-carboxylate (33.1 mg, 0.107 mmol) in a screw cap vial was added THF (1 mL) followed by 3 N aqueous solution of potassium phosphate, tribasic (0.089 mL, 0.267 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 6 h. The reaction mixture was cooled to room temperature, diluted with EtOAc (5 mL) and water (1 mL). The bottom aqueous layer was aspirated using a pipette. The organic layer was dried ($Na_2SO_4$), filtered and concentrated to obtain crude material. The crude residue was dissolved in MeOH (5 mL) was added 10% Pd-C (25 mg, 0.02 mmol) followed by ammonium formate (150 mg, 2.068 mmol). The vial was sealed and heated at 40° C. for 6 h. The reaction mixture was filtered through a pad of celite and the pad was rinsed with additional methanol. The filtrate was concentrated, dissolved in ethyl acetate (10 mL) and washed with water (2×2 mL), and sat. aq. NaCl solution (1×2), dried ($Na_2SO_4$), filtered and concentrated to obtain crude tert-butyl 4-(7-acetamido-9H-carbazol-3-yl)piperidine-1-carboxylate (7B), m/z (408, M+H).

Steps 3 and 4

The crude residue was dissolved in DCM (2 mL) and treated with TFA (1 mL) and the reaction mixture stirred for 1 h. The reaction mixture was concentrated and the crude product was subjected to HPLC purification. Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 4-minute hold at 100% B; Flow: 20 mL/min. Fractions containing the product were combined and dried via centrifugal evaporation to obtain N-(6-(piperidin-4-yl)-9H-carbazol-2-yl)acetamide (13 mg, 0.042 mmol, 47.5% yield, in 4 steps), m/z (308, M+H). HPLC $t_R$ 0.73 min (analytical HPLC Method F). $^1$H NMR (500 MHz, DMSO-$d_6$) δ 11.07 (s, 1H), 10.12 (s, 1H), 7.98-7.93 (m, 2H), 7.89-7.84 (m, 1H), 7.39-7.35 (m, 1H), 7.23-7.19 (m, 1H), 7.17-7.12 (m, 1H), 3.36-3.29 (m, 2H), 3.00-2.86 (m, 3H), 2.11 (s, 3H), 2.00-1.91 (m, 2H), 1.91-1.79 (m, 3H).

Example 8

2-(1-methyl-1H-pyrazol-4-yl)-6-(piperidin-4-yl)-9H-carbazole

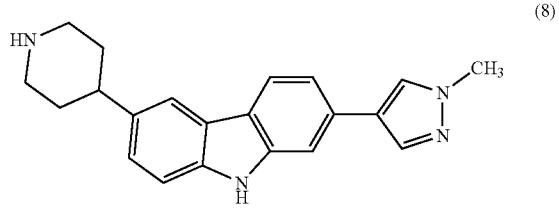 [SMILES: Cn1cc(-c2ccc3c(c2)[nH]c2ccc(C4CCNCC4)cc23)cn1]

(8)

Steps 1 to 3: tert-butyl 4-(7-(1-methyl-1H-pyrazol-4-yl)-9H-carbazol-3-yl)-5,6-dihydropyridine-1(2H)-carboxylate

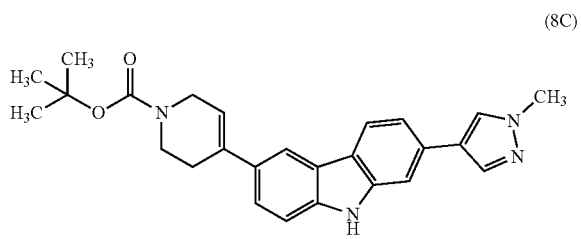 [SMILES: Cn1cc(-c2ccc3c(c2)[nH]c2ccc(C4=CCN(C(=O)OC(C)(C)C)CC4)cc23)cn1]

(8C)

To a mixture containing 2-bromo-6-chloro-9H-carbazole (50 mg, 0.178 mmol), 1-methyl-4-(4,4,5,5-tetramethyl-1,3,2-dioxaborolan-2-yl)-1H-pyrazole (40.8 mg, 0.196 mmol), and Xphos Pd G2 (3.51 mg, 4.46 µmol) in a screw cap vial was added THF (2 mL) followed by aqueous solution of potassium phosphate, tribasic (0.356 mL, 1.069 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 2 h. LCMS analysis displayed the formation of intermediate 6-chloro-2-(1-methyl-1H-pyrazol-4-yl)-9H-carbazole, m/z (282, M+H). The reaction mixture was cooled to room temperature and tert-butyl 4-(4,4,5,5-tetramethyl-1,3,2-dioxaborolan-2-yl)-5,6-dihydropyridine-1(2H)-carboxylate (60.6 mg, 0.196 mmol), and Xphos Pd G2 (3.51 mg, 4.46 µmol) was added. The system was evacuated under vacuum (via a needle from a nitrogen/vacuum manifold line) and backfilled with nitrogen gas. The procedure was repeated three times. The needle was removed and the vial was heated for additional 20 h at 55° C. The reaction mixture was cooled to room temperature, diluted with EtOAc (5 mL) and water (1 mL). The bottom aqueous layer was aspirated using a pipette. The organic layer was dried (Na$_2$SO$_4$), filtered and concentrated to obtain crude product. The crude product was dissolved in a small amount of DCM and charged to 4 g ISCO silica gel column and purified using the Teledyne ISCO system, eluting over a 10 min gradient with 0%-50% hexanes/ethyl acetate to obtain slightly impure tert-butyl 4-(7-(1-methyl-1H-pyrazol-4-yl)-9H-carbazol-3-yl)-5,6-dihydropyridine-1(2H)-carboxylate (8C) (60 mg, 55% yield), m/z (429, M+H).

Step 4: tert-butyl 4-(7-(1-methyl-1H-pyrazol-4-yl)-9H-carbazol-3-yl)piperidine-1-carboxylate

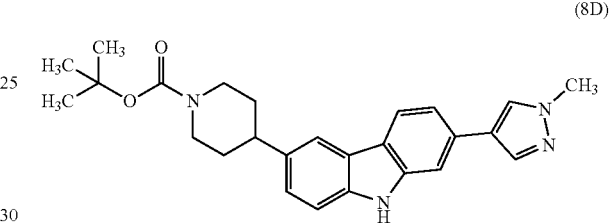

(8D)

A mixture containing tert-butyl 4-(7-(1-methyl-1H-pyrazol-4-yl)-9H-carbazol-3-yl)-5,6-dihydropyridine-1(2H)-carboxylate (50 mg, 0.117 mmol), 10% Pd-C (31.0 mg, 0.029 mmol) and ammonium formate (200 mg, 3.17 mmol) in MeOH (3 mL) was heated at 40° C. for 4 h. The reaction mixture was filtered through a plug of celite and concentrated to dryness. The residue was taken up in ethyl acetate (10 mL) and washed with water (2×2 mL) and sat. aq. NaCl solution (1×2 mL), dried (Na$_2$SO$_4$), filtered and concentrated to obtain crude tert-butyl 4-(7-(1-methyl-1H-pyrazol-4-yl)-9H-carbazol-3-yl)piperidine-1-carboxylate (8D).

Step 5

Crude tert-butyl 4-(7-(1-methyl-1H-pyrazol-4-yl)-9H-carbazol-3-yl)piperidine-1-carboxylate was treated with 50% TFA (2 mL) for 30 min and concentrated to dryness and subjected to HPLC purification. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation to obtain 2-(1-methyl-1H-pyrazol-4-yl)-6-(piperidin-4-yl)-9H-carbazole (19 mg, 0.055 mmol, 46.8% yield in two steps), m/z (331, M+H). HPLC $t_R$ 0.73 min (analytical HPLC Method F). $^1$H NMR (500 MHz, DMSO-$d_6$) δ 11.07 (s, 1H), 8.15-8.12 (m, 1H), 8.03 (d, J=7.9 Hz, 1H), 7.89 (br s, 2H), 7.59 (s, 1H), 7.42-7.38 (m, 1H), 7.37-7.33 (m, 1H), 7.27-7.21 (m, 1H), 3.87 (s, 3H), 3.25 (br m, 2H), 2.90-2.82 (m, 3H), 1.95-1.87 (m, 2H), 1.86-1.77 (m, 2H).

Example 9

6-(Piperidin-4-yl)-2-(pyridin-4-yl)-9H-carbazole

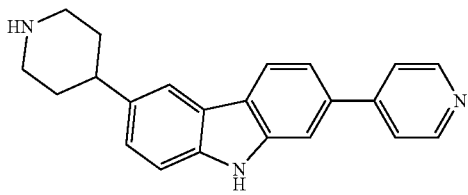
(9)

Steps 1 and 2: tert-butyl 4-(7-(pyridin-4-yl)-9H-carbazol-3-yl)-5,6-dihydropyridine-1(2H)-carboxylate

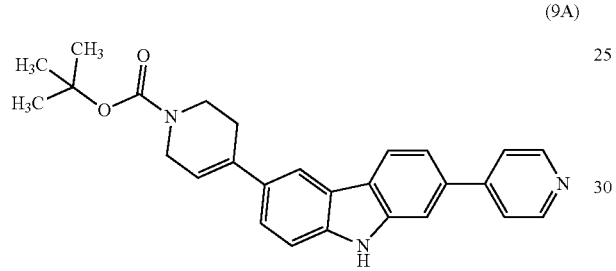
(9A)

To a mixture containing 4-bromopyridine, HCl (16.32 mg, 0.084 mmol), 6-chloro-2-(4,4,5,5-tetramethyl-1,3,2-dioxaborolan-2-yl)-9H-carbazole (25 mg, 0.076 mmol), and Xphos Pd G2 (1.501 mg, 1.908 µmol) in a screw cap vial was added THF (1 mL) followed by aqueous solution of 3 N potassium phosphate, tribasic (0.153 mL, 0.458 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 45° C. for 4 h. The reaction mixture was cooled to room temperature and tert-butyl 4-(4,4,5,5-tetramethyl-1,3,2-dioxaborolan-2-yl)-5,6-dihydropyridine-1(2H)-carboxylate (29.5 mg, 0.095 mmol) and additional amount of Xphos Pd G2 (1.501 mg, 1.908 µmol) was added. The vial was resealed and pump/purged and placed under nitrogen atmosphere and heated at 65° C. for 20 h. The reaction mixture was diluted with ethyl acetate (5 mL) and water (1 mL) and the bottom aqueous layer was decanted by aspiration using a pipette. The organic layer was filtered through a plug of celite and Na$_2$SO$_4$ reaction mixture and concentrated to dryness to obtain tert-butyl 4-(7-(pyridin-4-yl)-9H-carbazol-3-yl)-5,6-dihydropyridine-1(2H)-carboxylate (9A) (35 mg, crude), m/z (426, M+H).

Step 3

Tert-butyl 4-(7-(pyridin-4-yl)-9H-carbazol-3-yl)-5,6-dihydropyridine-1(2H)-carboxylate (35 mg, 0.082 mmol) was dissolved in TFA (2 mL) and stirred for 30 min. The reaction mixture was concentrated and the residue was subjected to HPLC purification. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation to obtain 2-(pyridin-4-yl)-6-(1,2,3,6-tetrahydropyridin-4-yl)-9H-carbazole (13 mg, 0.040 mmol, 48.6% yield), m/z (326.2, M+H). HPLC $t_R$ 0.66 min (analytical HPLC Method F). Partial $^1$H NMR (500 MHz, DMSO-d$_6$) δ 11.44-11.40 (m, 1H), 8.67 (br s, 2H), 8.31-8.26 (m, 1H), 8.25-8.20 (m, 1H), 7.88-7.77 (m, 3H), 7.63-7.53 (m, 2H), 7.52-7.45 (m, 1H), 6.24 (br s, 1H).

Example 10

1,3,4-trimethyl-5-(4-methyl-6-(piperidin-4-yl)-9H-carbazol-2-yl)pyridin-2(1H)-one

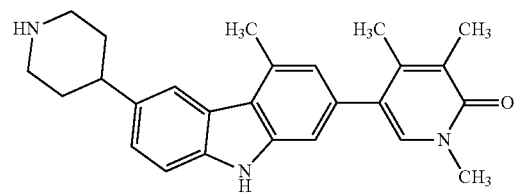
(10)

Step 1: 4-bromo-5'-chloro-2-methyl-2'-nitro-1,1'-biphenyl

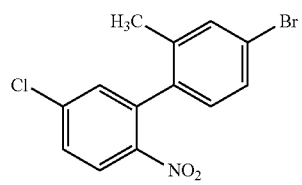
(10C)

To a mixture containing 2-bromo-4-chloro-1-nitrobenzene (100 mg, 0.423 mmol), (4-bromo-2-methylphenyl)boronic acid (100 mg, 0.465 mmol), and Pd(dppf)Cl$_2$ (15.47 mg, 0.021 mmol) in a screw cap vial was added THF (3 mL) followed by aqueous solution of 3 N potassium phosphate, tribasic (0.423 mL, 1.269 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 65° C. for 20 h. The reaction mixture was cooled to room temperature, diluted with EtOAc (10 mL) and water (2 mL). The reaction mixture was shaken and the bottom aqueous layer was aspirated out using a Pasteur pipette, dried (Na$_2$SO$_4$), filtered and concentrated to obtain crude material. The crude product was dissolved in a small amount of DCM and charged to 24 g ISCO silica gel column and purified using the Teledyne ISCO system, eluting over a 10 min gradient with 0%-10% hexanes/ethyl acetate to obtain 4-bromo-5'-chloro-2-methyl-2'-nitro-1,1'-biphenyl (10C) (130 mg, 85% pure). $^1$H NMR (400 MHz, DMSO-d$_6$)

δ 8.20-8.14 (m, 1H), 7.82-7.75 (m, 1H), 7.59 (dd, J=9.3, 2.0 Hz, 2H), 7.48-7.43 (m, 1H), 7.14-7.07 (m, 1H), 2.05 (s, 3H).

Step 2: 2-bromo-6-chloro-4-methyl-9H-carbazole

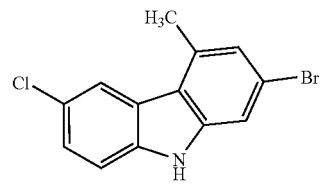

(10D)

A mixture containing 4-bromo-5'-chloro-2-methyl-2'-nitro-1,1'-biphenyl (130 mg, 0.398 mmol) and triphenylphosphine (261 mg, 0.995 mmol) was suspended in 1,2-dichlorobenzene (2 mL) in a 20 mL vial. The vial was purged and sealed under a nitrogen atmosphere and heated at 175° C. for 20 h. The reaction mixture was cooled to room temperature and charged to a 5 g dry silica gel ISCO pre-column, fitted to a 24 g ISCO silica gel Column and purified using the Teledyne ISCO system, eluting over a 15 min gradient with 0%-50% hexanes/ethyl acetate to obtain 2-bromo-6-chloro-4-methyl-9H-carbazole (10D) (100 mg, 0.339 mmol, 85% yield), m/z (295, M+H).

Step 3: 6-chloro-4-methyl-2-(4,4,5,5-tetramethyl-1,3,2-dioxaborolan-2-yl)-9H-carbazole

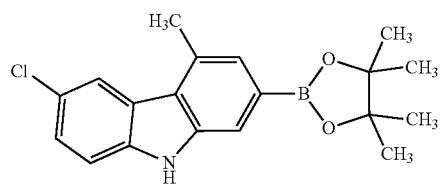

(10E)

To a mixture containing 2-bromo-6-chloro-4-methyl-9H-carbazole (0.5 g, 1.697 mmol), 4,4,4',4',5,5,5',5'-octamethyl-2,2'-bi(1,3,2-dioxaborolane) (0.539 g, 2.122 mmol), potassium acetate (0.500 g, 5.09 mmol) and Pd(dppf)Cl$_2$ (0.062 g, 0.085 mmol) in a screw cap vial was added DMF (5 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 85° C. for 20 h. The reaction mixture was cooled to room temperature, diluted with EtOAc (100 mL) and washed with aq. 10% LiCl solution (25 mL×2) and sat. aq. NaCl solution (25 mL), dried (Na$_2$SO$_4$), filtered and concentrated to obtain crude material. The residue was re-dissolved in DCM (20 mL), adsorbed to small amount of silica gel (10 g) and purified on the ISCO silica gel chromatography system using a 40 g ISCO silica gel column with Hex/EtOAc (0%-50%) over a 15 min gradient to obtain 6-chloro-4-methyl-2-(4,4,5,5-tetramethyl-1,3,2-dioxaborolan-2-yl)-9H-carbazole (10E) (400 mg, 1.171 mmol, 69.0% yield), m/z (342, M+H). $^1$H NMR (400 MHz, DMSO-d$_6$) δ 11.51-11.47 (m, 1H), 8.13-8.10 (m, 1H), 7.68 (s, 1H), 7.57 (d, J=8.7 Hz, 1H), 7.47-7.43 (m, 1H), 7.29 (s, 1H), 2.79 (s, 3H), 1.36-1.31 (m, 12H).

Steps 4 and 5: tert-butyl 4-(5-methyl-7-(1,4,5-trimethyl-6-oxo-1,6-dihydropyridin-3-yl)-9H-carbazol-3-yl)-5,6-dihydropyridine-1(2H)-carboxylate

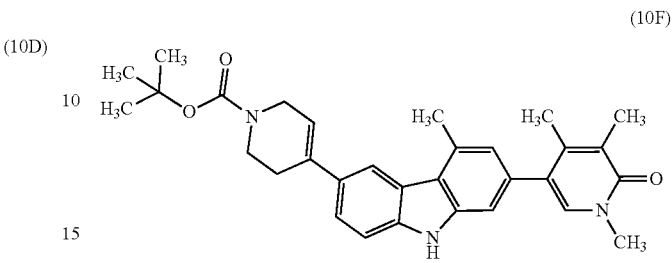

(10F)

To a mixture containing 6-chloro-4-methyl-2-(4,4,5,5-tetramethyl-1,3,2-dioxaborolan-2-yl)-9H-carbazole (50 mg, 0.146 mmol), 5-bromo-1,3,4-trimethylpyridin-2(1H)-one (33.2 mg, 0.154 mmol), and Xphos Pd G2 (2.88 mg, 3.66 µmol) in a screw cap vial was added THF (1 mL) followed by aqueous solution of potassium phosphate, tribasic (0.293 mL, 0.878 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 4 h. The reaction mixture was cooled to room temperature and tert-butyl 4-(4,4,5,5-tetramethyl-1,3,2-dioxaborolan-2-yl)-5,6-dihydropyridine-1(2H)-carboxylate (56.6 mg, 0.183 mmol) was added. The reaction mixture was capped and evacuated and backfilled with nitrogen gas and heated at 65° C. for 20 h. The reaction mixture was cooled to room temperature, diluted with EtOAc (5 mL) and water (1 mL) and the bottom aqueous layer was aspirated off using a pipette. The organic layer was dried (Na$_2$SO$_4$), filtered and concentrated to obtain crude product. The crude product was dissolved in a small amount of DCM and charged to 4 g ISCO silica gel column and purified using the Teledyne ISCO system, eluting over a 10 min gradient with 5%-100% hexanes/ethyl acetate to obtain tert-butyl 4-(5-methyl-7-(1,4,5-trimethyl-6-oxo-1,6-dihydropyridin-3-yl)-9H-carbazl-3-yl)-5,6-dihydropyridine-1(2H)-carboxylate (10F) (60 mg, 0.121 mmol, 82% yield), m/z (498, M+H).

Steps 6 and 7

To a solution containing tert-butyl 4-(5-methyl-7-(1,4,5-trimethyl-6-oxo-1,6-dihydropyridin-3-yl)-9H-carbazol-3-yl)-5,6-dihydropyridine-1(2H)-carboxylate (50 mg, 0.100 mmol) in MeOH (2 mL) were added ammonium formate (100 mg, 1.586 mmol) and 10% Pd-C (26.7 mg, 0.025 mmol). The vial was sealed and heated at 40° C. for 20 h. The reaction mixture was cooled to room temperature and filtered through a plug of celite and the celite pad rinsed with ethyl acetate (~10 mL). The filtrate was washed with water (2×2 mL) and sat. aq. NaCl solution (1 mL), dried (Na$_2$SO$_4$), filtered and concentrated to obtain tert-butyl 4-(5-methyl-7-(1,4,5-trimethyl-6-oxo-1,6-dihydropyridin-3-yl)-9H-carbazol-3-yl)piperidine-1-carboxylate, m/z (500, M+H).

Tert-butyl 4-(5-methyl-7-(1,4,5-trimethyl-6-oxo-1,6-dihydropyridin-3-yl)-9H-carbazol-3-yl)piperidine-1-carboxylate was dissolved in DCM (1 mL) and TFA (1 mL) was added. The reaction mixture was stirred for 30 min and concentrated to dryness. The residue was re-suspended in diethyl ether (~2 mL), sonicated in an ultrasonicator to obtain a white solid. The solid was filtered and washed with additional diethylether and dried to obtain 1,3,4-trimethyl-5-(4-methyl-6-(piperidin-4-yl)-9H-carbazol-2-yl)pyridin-2(1H)-one, TFA (10) (35 mg, 0.065 mmol, 64.4% yield), m/z (400 M+H). HPLC $t_R$ 0.65 min (analytical HPLC Method E). $^1$H NMR (400 MHz, METHANOL-$d_4$) δ 8.08-8.04 (m, 1H), 7.51-7.45 (m, 2H), 7.38-7.34 (m, 1H), 7.22-7.18 (m, 1H), 6.89-6.86 (m, 1H), 3.65 (s, 3H), 3.61-3.54 (m, 2H), 3.27-3.18 (m, 2H), 3.16-3.07 (m, 1H), 2.92-2.89 (s, 3H), 2.27-2.15 (m, 8H), 2.14-2.00 (m, 2H).

The Examples in Table 1 were prepared using a similar procedure used to prepare Example 10.

TABLE 1

| Ex. No. | Structure | Mol Wt | LCMS m/z obs. | HPLC $t_R$ (min) | HPLC method |
|---|---|---|---|---|---|
| 11 | 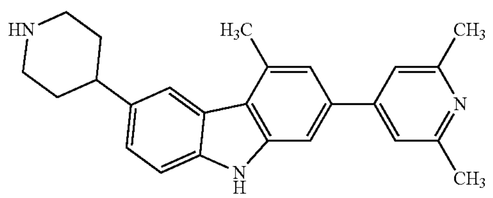 [SMILES: Cc1cc(-c2cc(C)c3c(c2)[nH]c2ccc(C4CCNCC4)cc23)cc(C)n1] | 369 | 370.2 | 0.56 | E |
| 12 | 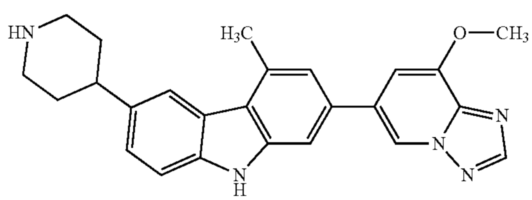 [SMILES: COc1cc(-c2cc(C)c3c(c2)[nH]c2ccc(C4CCNCC4)cc23)cn2ncnc12] | 411 | 412.3 | 1.08 | F |
| 13 | 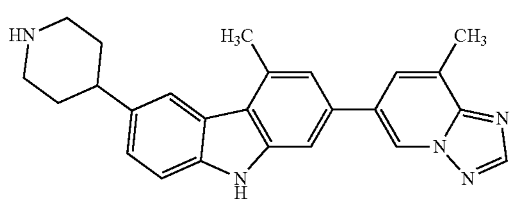 [SMILES: Cc1cc(-c2cc(C)c3ncnn3c2)cc2[nH]c3ccc(C4CCNCC4)cc3c12] | 395 | 396.3 | 1.12 | F |

Example 14

3-methyl-2-(8-methyl-[1,2,4]triazolo[1,5-a]pyridin-6-yl)-6-(piperidin-4-yl)-9H-carbazole (14)

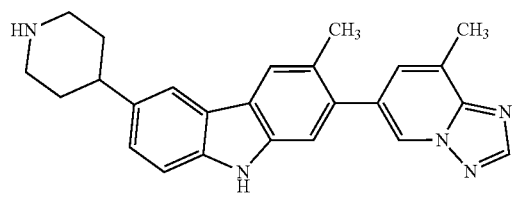

Step 1: 4'-chloro-3'-methyl-2-nitro-1,1'-biphenyl

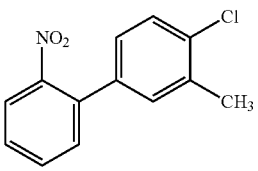

(14C)

To a mixture containing 1-bromo-2-nitrobenzene (889 mg, 4.40 mmol), (4-chloro-3-methylphenyl)boronic acid (750 mg, 4.40 mmol), and Pd(dppf)Cl$_2$ (81 mg, 0.110 mmol) in a screw cap vial was added THF (15 mL) followed by aqueous solution of potassium phosphate, tribasic (4.40 mL, 13.20 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 60° C. for 20 h. The reaction mixture was cooled to room temperature, diluted with EtOAc (50 mL) and the bottom aqueous layer was discarded and the organic layer was dried (Na₂SO₄), filtered and concentrated to obtain crude product. The crude product was dissolved in a small amount of DCM and charged to 40 g ISCO silica gel column and purified using the Teledyne ISCO system, eluting over a 20 min gradient with 0%-50% hexanes/ethyl acetate to obtain 4'-chloro-3'-methyl-2-nitro-1,1'-biphenyl (14C) (1.04 g, 4.20 mmol, 95% yield). ¹H NMR (400 MHz, DMSO-d₆) δ 8.03-7.99 (m, 1H), 7.81-7.75 (m, 1H), 7.68-7.62 (m, 1H), 7.58-7.54 (m, 1H), 7.50 (d, J=8.2 Hz, 1H), 7.37 (d, J=2.0 Hz, 1H), 7.20-7.15 (m, 1H), 2.37 (s, 3H).

Step 2: 2-chloro-3-methyl-9H-carbazole (14D) and 2-chloro-1-methyl-9H-carbazole (14E)

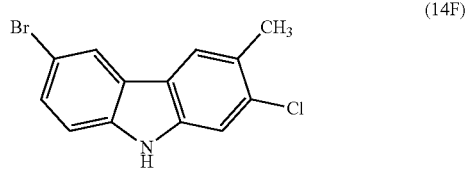 [SMILES: Cc1cc2c(cc1Cl)[nH]c1ccc(Br)cc12]

A solution containing 4'-chloro-3'-methyl-2-nitro-1,1'-biphenyl (1 g, 4.04 mmol) and triphenylphosphine (2.383 g, 9.08 mmol) in 1,2-dichlorobenzene (15 mL) was purged with nitrogen gas and heated at 180° C. under nitrogen for 20 h. The reaction mixture was cooled to room temperature and the solvent was removed in vacuo to obtain a slurry. The residue was purified via ISCO (0%-20, Hex/EtOAc; 80 g column). A mixture of 2-chloro-3-methyl-9H-carbazole (14D) and 2-chloro-1-methyl-9H-carbazole (14E) (800 mg, m/z (215, M+H) was isolated. ¹H NMR shows ~1/1 mixture of isomers.

Step 3

To a solution containing mixture of 2-chloro-3-methyl-9H-carbazole (450 mg, 2.086 mmol)/2-chloro-1-methyl-9H-carbazole in DMF (10 mL) was added a solution containing NBS (390 mg, 2.191 mmol) in DMF (5 mL) over a 30 min period. The reaction mixture was stirred for an additional 1 h, diluted with ethyl acetate (100 mL) and washed with aq. 10% LiCl (3×30 mL) and sat. aq. NaCl solution, dried (Na₂SO₄), filtered and concentrated. The reaction mixture was purified using SFC purification technique to obtain individual isomers. Preparative Conditions: Preparative Column: IC (5×25 cm, 5 μm); BPR pressure, 100 bars; temperature, 35° C.; flow rate, 350 mL/min; mobile phase, CO₂/MeOH (75/25); detector Wavelength, 220 nm. The product, 6-bromo-2-chloro-3-methyl-9H-carbazole (14F), eluted as the second peak (170 mg), m/z (294, M+H). The structure was confirmed using ¹H NMR. ¹H NMR (400 MHz, DMSO-d₆) δ 11.60-11.56 (m, 1H), 8.37 (d, J=1.7 Hz, 1H), 8.05-8.00 (m, 1H), 7.55-7.51 (m, 1H), 7.50-7.45 (m, 1H), 7.24-7.20 (m, 1H), 2.58 (s, 3H).

Step 4: tert-butyl 4-(7-chloro-6-methyl-9H-carbazol-3-yl)-3,6-dihydropyridine-1(2H)-carboxylate

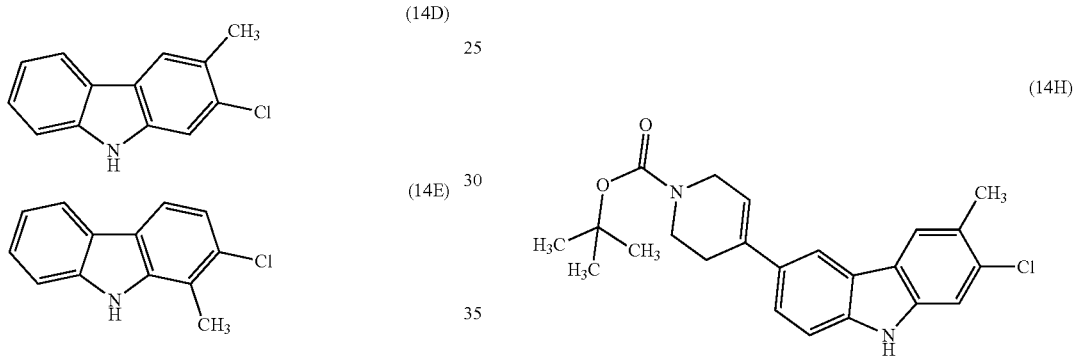

To a mixture containing 6-bromo-2-chloro-3-methyl-9H-carbazole (170 mg, 0.577 mmol), tert-butyl 4-(4,4,5,5-tetramethyl-1,3,2-dioxaborolan-2-yl)-3,6-dihydropyridine-1(2H)-carboxylate (187 mg, 0.606 mmol), and Pd(dppf)Cl₂ (10.56 mg, 0.014 mmol) in a screw cap vial was added THF (5 mL) followed by 3 N aqueous solution of potassium phosphate, tribasic (0.577 mL, 1.731 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 4 h. The reaction mixture was cooled to room temperature, diluted with EtOAc (20 mL) and water (2 mL) the bottom aqueous layer was removed using a pipette. The organic layer was dried (Na₂SO₄), filtered and concentrated to obtain crude product. The crude product was dissolved in a small amount of DCM and charged to 24 g ISCO silica gel column and purified using the Teledyne ISCO system, eluting over a 15 min gradient with 0%-30% hexanes/ethyl acetate to obtain tert-butyl 4-(7-chloro-6-methyl-9H-carbazol-3-yl)-3,6-dihydropyridine-1(2H)-carboxylate (14H) (159 mg, 69.4% yield), m/z (397, M+H).

Step 5a: 8-methyl-6-(4,4,5,5-tetramethyl-1,3,2-di-oxaborolan-2-yl)-[1,2,4]triazolo[1,5-a]pyridine

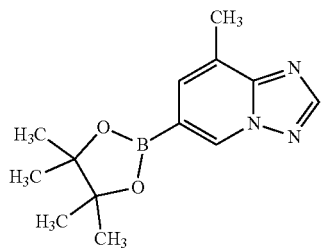
(14L)

To a mixture containing 6-bromo-8-methyl-[1,2,4]triazolo[1,5-a]pyridine (1 g, 4.72 mmol), 4,4,4',4',5,5,5',5'-octamethyl-2,2'-bi(1,3,2-dioxaborolane) (1.317 g, 5.19 mmol), potassium acetate (1.388 g, 14.15 mmol) and Pd(dppf)Cl$_2$(0.173 g, 0.236 mmol) in a screw cap vial was added dioxane (20 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 95° C. for 6 h. The reaction mixture was cooled to room temperature, diluted with EtOAc (100 mL) and washed with water (twice) and sat. aq. NaCl solution. The organic layer was dried (Na$_2$SO$_4$), filtered and concentrated to obtain crude product. The crude product was dissolved in a small amount of DCM and charged to 24 g ISCO silica gel Column and purified using the Teledyne ISCO system, eluting over a 15 min gradient with 5%-100% hexanes/ethyl acetate to obtain 8-methyl-6-(4,4,5,5-tetramethyl-1,3,2-dioxaborolan-2-yl)-[1,2,4]triazolo[1,5-a]pyridine (14L) (0.97 g, 3.74 mmol, 79% yield), ionizes as the boronic acid monomethyl ester, m/z (177.8/179). $^1$H NMR (400 MHz, DMSO-d$_6$) δ 8.81-8.78 (m, 1H), 8.51 (s, 1H), 7.57 (d, J=1.0 Hz, 1H), 2.59-2.54 (m, 3H), 1.37-1.32 (m, 12H).

Step 5b: 1,3,4-trimethyl-5-(4,4,5,5-tetramethyl-1,3,2-dioxaborolan-2-yl)pyridin-2(1H)-one

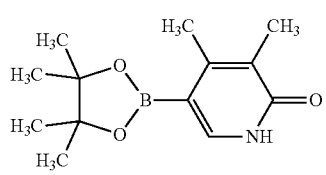
(14N)

To a mixture containing 5-bromo-1,3,4-trimethylpyridin-2(1H)-one (275 mg, 1.273 mmol), bis(pinacolato)diboron (372 mg, 1.464 mmol), potassium acetate (375 mg, 3.82 mmol) and Pd(dppf)Cl$_2$ (46.6 mg, 0.064 mmol) in a screw cap vial was added 1,4-dioxane (5 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 90° C. for 20 h. The reaction mixture was cooled to room temperature, diluted with EtOAc (20 mL) and filtered through a pad of celite. The filtered and concentrated the crude residue was re-dissolved in DCM (20 mL), adsorbed to small amount of silica gel (5 g) and purified on the ISCO silica gel chromatography system using a 12 g ISCO silica gel column with Hex/EtOAc (5%-100%) over a 10 min gradient to obtain 1,3,4-trimethyl-5-(4,4,5,5-tetramethyl-1,3,2-dioxaborolan-2-yl)pyridin-2 (1H)-one (14N) (200 mg, 0.760 mmol, 59.7% yield), m/z (264, M+H). $^1$H NMR (400 MHz, CHLOROFORM-d) δ 7.66 (s, 1H), 3.61-3.51 (s, 3H), 2.36 (s, 3H), 2.13 (br s, 3H), 1.35-1.31 (m, 12H).

Step 5c: 8-methoxy-6-(4,4,5,5-tetramethyl-1,3,2-dioxaborolan-2-yl)-[1,2,4]triazolo[1,5-a] pyridine

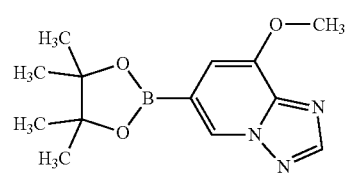
(14P)

To a mixture containing 6-bromo-8-methoxy-[1,2,4]triazolo[1,5-a]pyridine (1 g, 4.39 mmol), 4,4,4',4',5,5,5',5'-octamethyl-2,2'-bi(1,3,2-dioxaborolane) (1.225 g, 4.82 mmol), potassium acetate (1.291 g, 13.16 mmol) and Pd(dppf)Cl$_2$ (0.160 g, 0.219 mmol) in a screw cap vial was added dioxane (20 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 95° C. for 6 h. The reaction mixture was cooled to room temperature, diluted with EtOAc (100 mL) and washed with water twice and sat. aq. NaCl solution. The organic layer was dried (Na$_2$SO$_4$), filtered and concentrated to obtain crude material. The crude product was suspended in hexanes/ether (~100 mL, 9/1), sonicated using a ultrasonicator for 30 min and filtered through a pad of celite. The solids were rinsed with additional hexanes/ether and the yellow filtrate was concentrated to obtain 8-methoxy-6-(4,4,5,5-tetramethyl-1,3,2-dioxaborolan-2-yl)-[1,2,4]triazolo[1,5-a]pyridine (14P) (1 g, 3.63 mmol, 83% yield), ionize on LCMS as the boronic acid ester, m/z (193). $^1$H NMR (400 MHz, DMSO-d$_6$) δ 8.59-8.54 (m, 1H), 8.51-8.47 (m, 1H), 7.02 (s, 1H), 4.02 (s, 3H), 1.35 (s, 12H).

Step 5: tert-butyl 4-(6-methyl-7-(8-methyl-[1,2,4] triazolo[1,5-a]pyridin-6-yl)-9H-carbazol-3-yl)-3,6-dihydropyridine-1(2H)-carboxylate

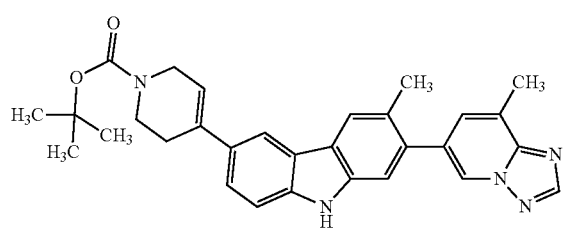
(14I)

To a mixture containing 8-methyl-6-(4,4,5,5-tetramethyl-1,3,2-dioxaborolan-2-yl)-[1,2,4]triazolo[1,5-a]pyridine (23.50 mg, 0.091 mmol), tert-butyl 4-(7-chloro-6-methyl-9H-carbazol-3-yl)-3,6-dihydropyridine-1(2H)-carboxylate (30 mg, 0.076 mmol), and Xphos Pd G2 (1.487 mg, 1.890 µmol) in a screw cap vial was added THF (1 mL) followed by 3N aqueous solution of potassium phosphate, tribasic (0.076 mL, 0.227 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 55° C. for 4 h. The reaction mixture was cooled to room temperature, diluted with EtOAc (5 mL) and the bottom aqueous layer was removed by using a pipette. The organic layer was dried ($Na_2SO_4$), filtered and concentrated to obtain crude product. The crude product was dissolved in a small amount of DCM and charged to 4 g ISCO silica gel column and purified using the Teledyne ISCO system, eluting over a 10 min gradient with 5%-100% hexanes/ethyl acetate to obtain tert-butyl 4-(6-methyl-7-(8-methyl-[1,2,4]triazolo[1,5-a]pyridin-6-yl)-9H-carbazol-3-yl)-3,6-dihydropyridine-1(2H)-carboxylate (14I) (28 mg, 0.057 mmol, 75% yield), m/z (494, M+H).

Step 6: tert-butyl 4-(6-methyl-7-(8-methyl-[1,2,4]triazolo[1,5-a]pyridin-6-yl)-9H-carbazol-3-yl)piperidine-1-carboxylate (14J)

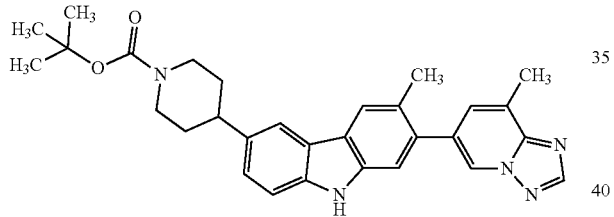

To a solution containing tert-butyl 4-(6-methyl-7-(8-methyl-[1,2,4]triazolo[1,5-a]pyridin-6-yl)-9H-carbazol-3-yl)-3,6-dihydropyridine-1(2H)-carboxylate (28 mg, 0.057 mmol) in MeOH (4 mL) was added ammonium formate (500 mg, 7.93 mmol) followed by the addition of $Pd(OH)_2$ (15 mg, 0.021 mmol). The reaction mixture was sealed in a 40 mL vial that was fitted with a Teflon lined pressure-relief septum cap and heated at 55° C. The reaction mixture was cooled to room temperature and diluted with ethyl acetate (20 mL) and filtered through a pad of celite. The filtrate was washed with water (2×5 mL) and sat. aq. NaCl solution (1×5 mL), dried ($Na_2SO_4$), filtered and concentrated. The crude product was dissolved in a small amount of DCM and charged to 4 g ISCO silica gel column and purified using the Teledyne ISCO system, eluting over a 10 min gradient with 5%-100% hexanes/ethyl acetate to obtain tert-butyl 4-(6-methyl-7-(8-methyl-[1,2,4]triazolo[1,5-a]pyridin-6-yl)-9H-carbazol-3-yl)piperidine-1-carboxylate (14J) (25 mg, 0.050 mmol, 89% yield), m/z (496, M+H).

Step 7

To a solution containing tert-butyl 4-(6-methyl-7-(8-methyl-[1,2,4]triazolo[1,5-a]pyridin-6-yl)-9H-carbazol-3-yl)piperidine-1-carboxylate (20 mg, 0.040 mmol) in DCM (1 mL) was added TFA (1 mL, 12.98 mmol). The reaction mixture was stirred for 30 min and concentrated to dryness. The residue was suspended in diethylether (2 mL) and sonicated till a fine powder was obtained. The solids were filtered and rinsed with additional diethyl ether and dried to obtain 3-methyl-2-(8-methyl-[1,2,4]triazolo[1,5-a]pyridin-6-yl)-6-(piperidin-4-yl)-9H-carbazole, TFA (20 mg, 0.037 mmol, 92% yield), m/z (396, M+H). HPLC $t_R$ 0.67 min (analytical HPLC Method E). $^1$H NMR (400 MHz, METHANOL-$d_4$) δ 8.69-8.65 (m, 1H), 8.51-8.47 (m, 1H), 8.05-7.99 (m, 2H), 7.63-7.60 (m, 1H), 7.47-7.43 (m, 1H), 7.42-7.38 (m, 1H), 7.36-7.30 (m, 1H), 3.62-3.54 (m, 2H), 3.29-3.18 (m, 2H), 3.17-3.04 (m, 1H), 2.73-2.69 (s, 3H), 2.46 (s, 3H), 2.26-2.17 (m, 2H), 2.13-1.99 (m, 2H).

Example 15

2-(8-Methoxy-[1,2,4]triazolo[1,5-a]pyridin-6-yl)-3,4-dimethyl-6-(piperidin-4-yl)-9H-carbazole (15)

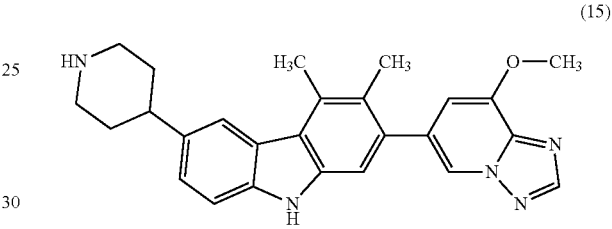

Step 1: 2-(4-bromo-2,3-dimethylphenyl)-4,4,5,5-tetramethyl-1,3,2-dioxaborolane (15B)

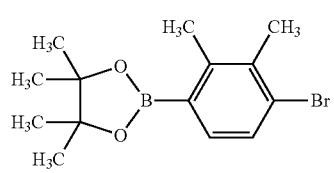

To a solution containing 1-bromo-4-iodo-2,3-dimethylbenzene (975 mg, 3.14 mmol) in THF (20 mL), cooled to −78° C. in a dry ice acetone bath, was added dropwise BuLi (1.380 mL, 3.45 mmol). The reaction mixture was stirred for 30 min and 2-isopropoxy-4,4,5,5-tetramethyl-1,3,2-dioxaborolane (0.768 mL, 3.76 mmol) was added dropwise. The reaction mixture was stirred for an additional 30 min at −78° C. and warmed to approximately −10° C. for 1 h. The reaction mixture was quenched with saturated ammonium chloride (5 mL). The reaction mixture was diluted with ethyl acetate (100 mL) and washed with water (2×20 mL) and sat. aq. NaCl solution (1×20 mL), dried ($Na_2SO_4$), filtered and concentrated. The crude product was dissolved in a small amount of DCM and charged to 24 g ISCO silica gel Column and purified using the Teledyne ISCO system, eluting over a 15 min gradient with 0%-30% hexanes/ethyl acetate to obtain 2-(4-bromo-2,3-dimethylphenyl)-4,4,5,5-tetramethyl-1,3,2-dioxaborolane (15B) (620 mg, 1.993 mmol, 63.6% yield. $^1$H NMR (400 MHz, CHLOROFORM-d) δ 7.48-7.38 (m, 1H), 7.30-7.27 (m, 1H), 2.56 (s, 3H), 2.41 (s, 3H), 1.37 (s, 12H).

Step 2: 4-bromo-5'-chloro-2,3-dimethyl-2'-nitro-1,1'-biphenyl

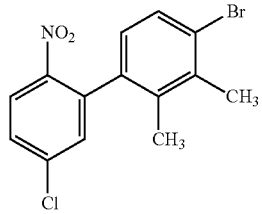

(15D)

To a mixture containing 2-(4-bromo-2,3-dimethylphenyl)-4,4,5,5-tetramethyl-1,3,2-dioxaborolane (600 mg, 1.929 mmol), 2-bromo-4-chloro-1-nitrobenzene (502 mg, 2.122 mmol), and Pd(dppf)Cl$_2$ (70.6 mg, 0.096 mmol) in a screw cap vial was added THF (7.5 mL) followed by 3 N aqueous solution of potassium phosphate, tribasic (0.643 mL, 1.929 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 60° C. for 20 h. The reaction mixture was cooled to room temperature, diluted with EtOAc (25 mL) and water (2 mL) the bottom aqueous layer was aspirated using a pipette. The organic layer was dried (Na$_2$SO$_4$), filtered and concentrated to obtain crude product. The crude product was dissolved in a small amount of DCM and charged to 24 g ISCO silica gel Column and purified using the Teledyne ISCO system, eluting over a 15 min gradient with 0%-30% hexanes/ethyl acetate to obtain 4-bromo-5'-chloro-2,3-dimethyl-2'-nitro-1,1'-biphenyl (15D) (620 mg, ~85% purity). $^1$H NMR (400 MHz, CHLOROFORM-d) δ 8.01 (d, J=8.7 Hz, 1H), 7.56-7.50 (m, 1H), 7.49-7.44 (m, 1H), 7.33-7.30 (m, 1H), 6.85-6.79 (m, 1H), 2.47-2.44 (3, 3H), 2.09 (s, 3H).

Step 3: 2-bromo-6-chloro-3,4-dimethyl-9H-carbazole

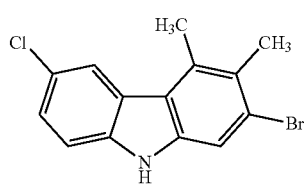

(15E)

A solution containing 4-bromo-5'-chloro-2,3-dimethyl-2'-nitro-1,1'-biphenyl (620 mg, 1.820 mmol) and triphenylphosphine (1194 mg, 4.55 mmol) in 1,2-dichlorobenzene (10 mL) was heated at 170° C. under a nitrogen atmosphere for 16 h. The reaction mixture was cooled to room temperature and concentrated. The residue was re-dissolved in DCM (50 mL), adsorbed to small amount of silica gel (10 g) and purified on the ISCO silica gel chromatography system using a 40 g ISCO silica gel column with hexanes/ethyl acetate (0%-30%) over a 20 min gradient to obtain 2-bromo-6-chloro-3,4-dimethyl-9H-carbazole (15E) (150 mg, 85% purity), m/z (308, M-H)$^-$.

Step 4: 6-chloro-2-(8-methoxy-[1,2,4]triazolo[1,5-a]pyridin-6-yl)-3,4-dimethyl-9H-carbazole

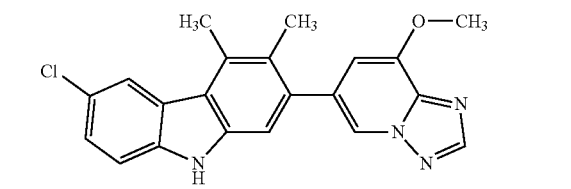

(15F)

To a mixture containing crude 2-bromo-6-chloro-3,4-dimethyl-9H-carbazole (40 mg, 0.130 mmol), 8-methoxy-6-(4,4,5,5-tetramethyl-1,3,2-dioxaborolan-2-yl)-[1,2,4]triazolo[1,5-a] pyridine (37.4 mg, 0.136 mmol) and Pd(dppf)Cl$_2$ (4.74 mg, 6.48 µmol) in a screw cap vial was added THF (1.5 mL) followed by aqueous solution of potassium phosphate, tribasic (0.130 mL, 0.389 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 60° C. for 20 h. The reaction mixture was cooled to room temperature, diluted with EtOAc (5 mL) and the bottom aqueous layer was aspirated using a pipette. The organic layer was dried (Na$_2$SO$_4$), filtered and concentrated to obtain crude product. The crude product was dissolved in a small amount of DCM and charged to 4 g ISCO silica gel column and purified using the Teledyne ISCO system, eluting over a 10 min gradient with 0%-100% hexanes/ethyl acetate to obtain 6-chloro-2-(8-methoxy-[1,2,4]triazolo[1,5-a]pyridin-6-yl)-3,4-dimethyl-9H-carbazole (15F) (50 mg), m/z (377, M+H). The material is contaminated with an impurity. This was used as such in the next step.

Step 5: tert-butyl 4-(7-(8-methoxy-[1,2,4]triazolo[1,5-a]pyridin-6-yl)-5,6-dimethyl-9H-carbazol-3-yl)-3,6-dihydropyridine-1(2H)-carboxylate

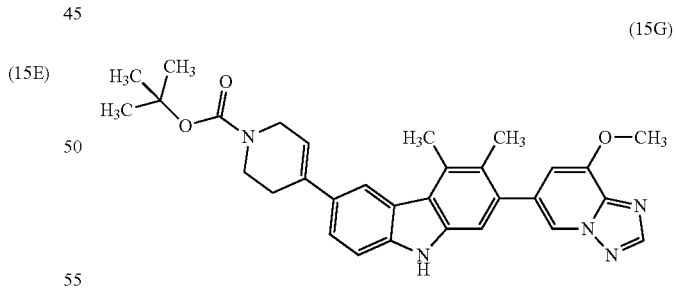

(15G)

To a reaction mixture containing 6-chloro-2-(8-methoxy-[1,2,4]triazolo[1,5-a]pyridin-6-yl)-3,4-dimethyl-9H-carbazole (~50 mg, crude) Xphos Pd G2 (2.55 mg, 3.24 µmol), and tert-butyl 4-(4,4,5,5-tetramethyl-1,3,2-dioxaborolan-2-yl)-3,6-dihydropyridine-1(2H)-carboxylate (44.1 mg, 0.143 mmol) in a screw cap vial was added THF (1.5 mL) followed by 3N aqueous solution of potassium phosphate, tribasic (0.130 mL, 0.389 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 60° C. for 20 h. The reaction mixture was cooled to room temperature, diluted with EtOAc (5 mL) and the bottom aqueous layer was aspirated using a pipette. The organic layer was dried ($Na_2SO_4$), filtered and concentrated to obtain crude product. The crude product was dissolved in a small amount of DCM and charged to 4 g ISCO silica gel column and purified using the Teledyne ISCO system, eluting over a 10 min gradient with 0%-100% hexanes/ethyl acetate to obtain tert-butyl 4-(7-(8-methoxy-[1,2,4]triazolo[1,5-a]pyridin-6-yl)-5,6-dimethyl-9H-carbazol-3-yl)-3,6-dihydropyridine-1(2H)-carboxylate (15G) (31 mg, ~85% purity), m/z (524, M+H).

Step 6: tert-butyl 4-(7-(8-methoxy-[1,2,4]triazolo[1,5-a]pyridin-6-yl)-5,6-dimethyl-9H-carbazol-3-yl)piperidine-1-carboxylate (15H)

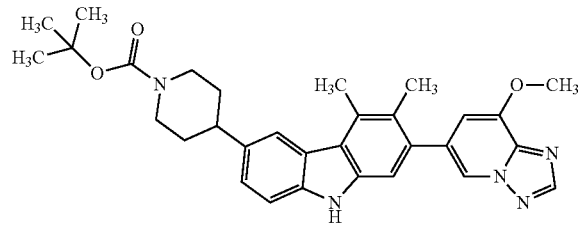

To a solution containing tert-butyl 4-(7-(8-methoxy-[1,2,4]triazolo[1,5-a]pyridin-6-yl)-5,6-dimethyl-9H-carbazol-3-yl)-3,6-dihydropyridine-1(2H)-carboxylate (30 mg, 0.057 mmol) in MeOH (3 mL) was added ammonium formate (250 mg, 3.96 mmol) followed by the addition of $Pd(OH)_2$ (15 mg, 0.021 mmol). The reaction mixture was stirred for and heated at 55° C. for 20 h. The reaction mixture was cooled to room temperature, diluted with ethyl acetate (20 mL) and filtered through a pad of celite. The filtrate was washed with water (2×5 mL) and sat. aq. NaCl solution (5 mL), dried ($Na_2SO_4$), filtered and concentrated. The crude product was dissolved in a small amount of DCM and charged to 4 g ISCO silica gel column and purified using the Teledyne ISCO system, eluting over a 10 min gradient with 5%-100% hexanes/ethyl acetate to obtain impure tert-butyl 4-(7-(8-methoxy-[1,2,4]triazolo[1,5-a]pyridin-6-yl)-5,6-dimethyl-9H-carbazol-3-yl)piperidine-1-carboxylate (15H) (26 mg), m/z (526, M+H).

Step 7

A solution containing tert-butyl 4-(7-(8-methoxy-[1,2,4]triazolo[1,5-a]pyridin-6-yl)-5,6-dimethyl-9H-carbazol-3-yl)piperidine-1-carboxylate (30 mg, 0.057 mmol) in DCM (1 mL) was treated with TFA (0.5 mL, 6.49 mmol) and stirred for 30 min. The reaction mixture was concentrated to dryness and the residue was subjected to HPLC purification. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 6-46% B over 20 minutes, then a 4-minute hold at 100% B; Flow: 20 mL/min. Fractions containing the product were combined and dried via centrifugal evaporation to obtain 2-(8-methoxy-[1,2,4]triazolo[1,5-a]pyridin-6-yl)-3,4-dimethyl-6-(piperidin-4-yl)-9H-carbazole, TFA (18 mg, 0.033 mmol, 58.5% yield), m/z (426, M+H). HPLC $t_R$ 1.1 min (analytical HPLC Method F). $^1$H NMR (500 MHz, DMSO-$d_6$) δ 11.27-11.21 (m, 1H), 8.58-8.53 (m, 1H), 8.50-8.47 (m, 1H), 8.12-8.05 (m, 1H), 7.53-7.46 (m, 1H), 7.35-7.25 (m, 2H), 7.12-7.05 (m, 1H), 4.03 (s, 3H), 3.48-3.40 (m, 1H), 3.15-2.99 (m, 4H), 2.87-2.85 (m, 3H), 2.34 (s, 3H), 2.10-1.90 (m, 4H).

The Examples in Table 2 were prepared using a similar procedure used to prepare Example 15.

TABLE 2

| Ex. No. | Structure | Mol Wt | LCMS m/z obs. | HPLC $t_R$ (min) | HPLC method |
|---|---|---|---|---|---|
| 16 | 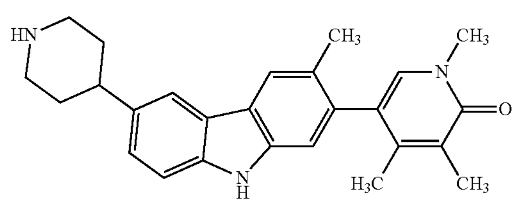 [SMILES: Cc1cc2c(cc1-c1cn(C)c(=O)c(C)c1C)[nH]c1ccc(C3CCNCC3)cc12] | 399 | 400.0 | 0.65 | E |
| 17 | 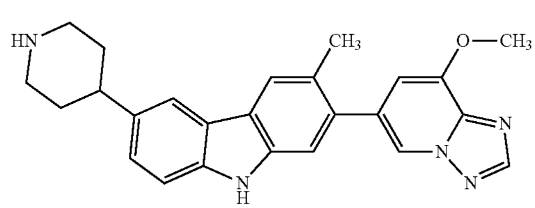 [SMILES: COc1cc(-c2cc3[nH]c4ccc(C5CCNCC5)cc4c3cc2C)cn2ncnc12] | 411 | 412.1 | 0.65 | E |

Example 18

5-(6-(1-(2-Hydroxy-2-methylpropyl)piperidin-4-yl)-4-methyl-9H-carbazol-2-yl)-1,3,4-trimethylpyridin-2(1H)-one

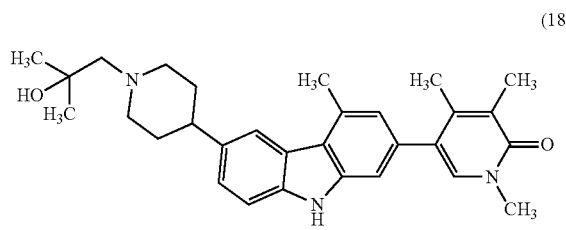

(18)

To a solution containing 1,3,4-trimethyl-5-(4-methyl-6-(piperidin-4-yl)-9H-carbazol-2-yl)pyridin-2(1H)-one, TFA (15 mg, 0.029 mmol) and TEA (20 μL, 0.143 mmol) in MeOH (1 mL) was added 2,2-dimethyloxirane (20 mg, 0.277 mmol). The reaction mixture was stirred for 20 h and concentrated. The residue was suspended in water ~2 mL and sonicated in a ultra sonicator for 20 min till a fine powder was formed. The solids were filtered and rinsed with additional water and dried to obtain 5-(6-(1(2-hydroxy-2-methylpropyl)piperidin-4-yl)-4-methyl-9H-carbazol-2-yl)-1,3,4-trimethylpyridin-2(1H)-one (10 mg, 0.020 mmol, 69.0% yield), m/z (472, M+H). HPLC $t_R$ 0.68 min (analytical HPLC Method E). $^1$H NMR (400 MHz, METHANOL-$d_4$) δ 8.05(s, 1H), 7.48 (s, 1H), 7.45-7.40 (m, 1H), 7.36-7.31 (m, 1H), 7.18(s, 1H), 6.85 (s, 1H), 3.65 (s, 3H), 3.27-3.12 (m, 2H), 2.90 (s, 3H), 2.80-2.64 (m, 1H), 2.56-2.38 (m, 4H), 2.24 (s, 3H), 2.18 (s, 3H), 2.10-1.96 (m, 2H), 1.96-1.84 (m, 2H), 1.31-1.25 (s, 6H).

The Examples in Table 3 were prepared using a similar procedure used to prepare Example 18.

TABLE 3

| Ex. No. | Structure | Mol Wt | LCMS m/z obs. | HPLC $t_R$ (min) | HPLC method |
|---|---|---|---|---|---|
| 19 | 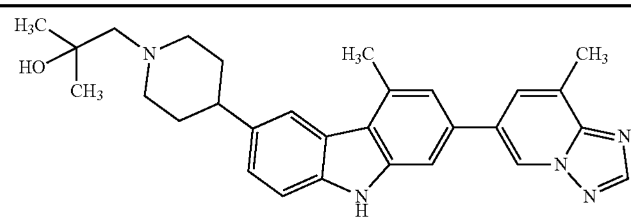 | 467.6 | 468.2 | 0.69 | E |
| 20 | 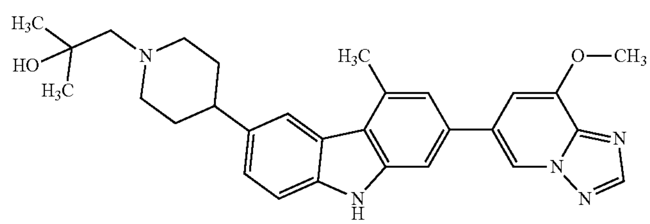 [SMILES: COc1cc(-c2cc(C)c3c(c2)[nH]c2ccc(C4CCN(CC(C)(C)O)CC4)cc23)cn2ncnc12] | 483.6 | 484.2 | 0.68 | E |
| 21 | 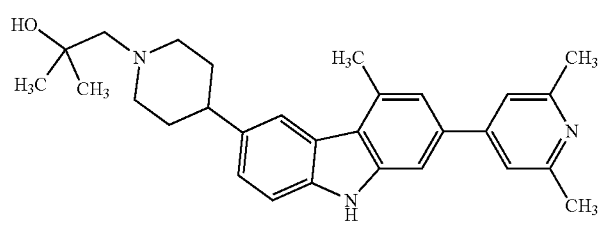 [SMILES: Cc1cc(-c2cc(C)c3c(c2)[nH]c2ccc(C4CCN(CC(C)(C)O)CC4)cc23)cc(C)n1] | 441.6 | 442.2 | 0.54 | E |
| 22 | 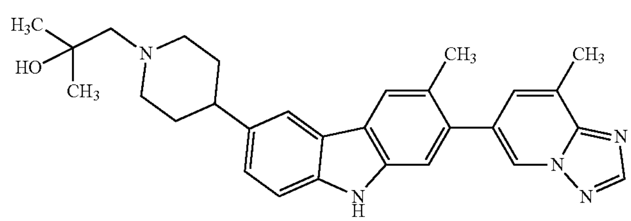 [SMILES: Cc1cc2c(cc1-c1cc(C)c3ncnn3c1)[nH]c1ccc(C3CCN(CC(C)(C)O)CC3)cc12] | 467.6 | 468.3 | 0.69 | E |
| 23 | 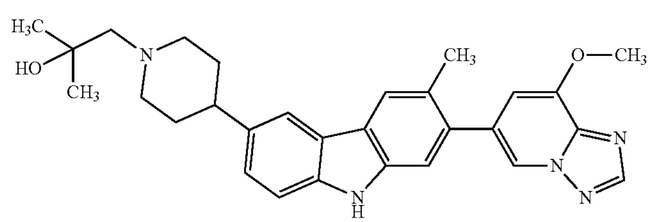 [SMILES: COc1cc(-c2cc3[nH]c4ccc(C5CCN(CC(C)(C)O)CC5)cc4c3cc2C)cn2ncnc12] | 483.2 | 484.2 | 0.67 | E |

TABLE 3-continued

| Ex. No. | Structure | Mol Wt | LCMS m/z obs. | HPLC $t_R$ (min) | HPLC method |
|---|---|---|---|---|---|
| 24 | 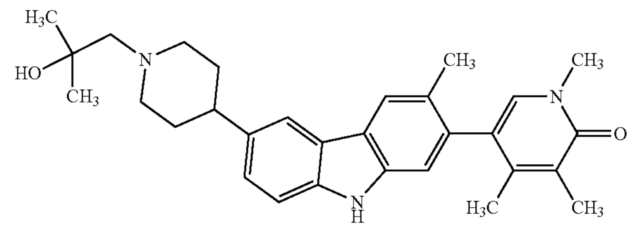 [SMILES: Cc1cc2c(cc1-c1cn(C)c(=O)c(C)c1C)[nH]c1ccc(C3CCN(CC(C)(C)O)CC3)cc12] | 471.6 | 472.2 | 0.67 | E |
| 25 | 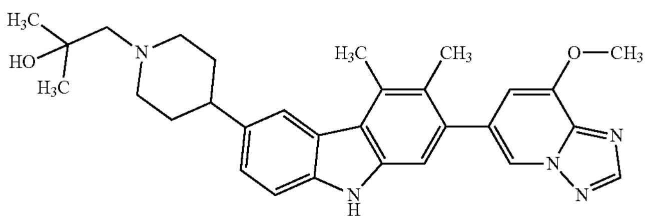 [SMILES: COc1cc(-c2cc3[nH]c4ccc(C5CCN(CC(C)(C)O)CC5)cc4c3c(C)c2C)cn2ncnc12] | 497.6 | 498.2 | 0.70 | E |

Example 26

2-(8-methoxy-[1,2,4]triazolo[1,5-a]pyridin-6-yl)-3,4-dimethyl-6-(piperidin-3-yl)-9H-carbazole (26)

Example 27

2-(dimethylamino)-1-(3-(7-(8-methoxy-[1,2,4]triazolo[1,5-a]pyridin-6-yl)-5,6-dimethyl-9H-carbazol-3-yl)piperidin-1-yl)ethan-1-one

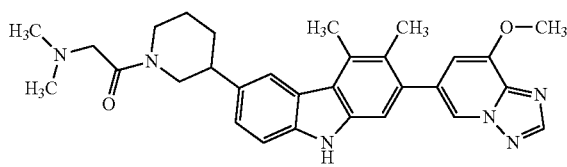

(27)

Step 1: 4-chloro-2,3-dimethylphenol

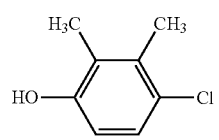

(26A)

To a solution of 2,3-dimethylphenol (204 mg, 1.67 mmol) in acetonitrile (16.7 mL) at room temperature was added pTsOH (635 mg, 3.34 mmol). Upon complete dissolution, this was followed by the addition of N-chlorosuccinimide (223 mg, 1.67 mmol) in a single portion. After 2 h, another aliquot of N-chlorosuccinimide (32 mg, 0.240 mmol) was added. The reaction mixture was stirred for 1 h more and then diluted with water and excess solid $Na_2SO_3$ was added to quench excess reagent. The reaction mixture was diluted with EtOAc, and the aqueous layer was extracted three times with EtOAc. The organic layer was dried over sodium sulfate, filtered, and concentrated to obtain a crude white solid. This material was taken up in DCM and loaded onto a silica gel for purification by column chromatography eluting in Hex/DCM 0-70% and then Hex/EtOAc 0-100% to obtain 4-chloro-2,3-dimethylphenol (220 mg, 1.41 mmol, 84% yield). HPLC $t_R$ 0.85 min (analytical HPLC Method TS1). $^1$H NMR (499 MHz, CHLOROFORM-d) δ 7.06 (d, J=8.5 Hz, 1H), 6.58 (d, J=8.7 Hz, 1H), 4.70 (br s, 1H), 2.33 (s, 3H), 2.20 (s, 3H).

Step 2: 4-chloro-2,3-dimethylphenyl trifluoromethane sulfonate

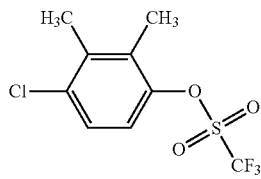
(26B)

To a solution of 4-chloro-2,3-dimethylphenol (1 g, 6.39 mmol), and Et₃N (2.67 ml, 19.2 mmol) in DCM (42.6 mL) cooled to 0° C. was added Tf₂O (1.40 mL, 8.30 mmol). The mixture was slowly warmed to room temperature. After 2 h, the reaction was quenched by the addition of water and DCM. The aqueous layer was extracted with DCM, and the combined organic layer was dried over sodium sulfate, filtered, and concentrated. The crude material was dissolved in toluene and loaded onto silica gel for purification by silica gel column chromatography eluting in Hex/EtOAc 0-40% to obtain 4-chloro-2,3-dimethylphenyl trifluoromethane sulfonate (1.27 g, 68.9% yield). HPLC $t_R$ 1.07 min (analytical HPLC Method TS1). $^1$H NMR (499 MHz, CHLOROFORM-d) δ 7.28 (d, J=9.0 Hz, 1H), 7.06 (d, J=8.8 Hz, 1H), 2.39 (s, 3H), 2.33 (s, 3H).

Step 3: 2-(4-chloro-2,3-dimethylphenyl)-4,4,5,5-tetramethyl-1,3,2-dioxaborolane

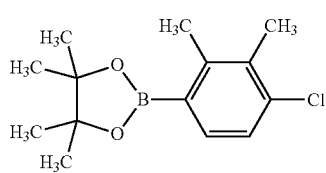
(26C)

A solution of 4-chloro-2,3-dimethylphenyl trifluoromethane sulfonate (1.00 g, 3.46 mmol), 4,4,4', 4', 5,5,5', 5'-octamethyl-2,2'-bi(1,3,2-dioxaborolane) (1.41 g, 5.54 mmol), potassium acetate (1.02 g, 10.4 mmol), and PdCl₂(dppf) (0.127 g, 0.173 mmol) in 1,4-dioxane (23.1 mL) was degassed with nitrogen for 10 min. The reaction mixture was sealed and stirred at 100° C. for 15 h. Upon completion, the reaction mixture was diluted with DCM and filtered. A duplicate reaction mixture of identical scale was run and then both mixtures were combined. The crude filtrate was concentrate, redissolved in DCM, triturated, and filtered again to obtain a brown oil upon concentration of the filtrate. This material was taken up in toluene and loaded onto silica gel for purification by column chromatography eluting with Hex/DCM 0-50% to obtain 2-(4-chloro-2,3-dimethylphenyl)-4,4,5,5-tetramethyl-1,3,2-dioxaborolane (1.42 g, 5.32 mmol). HPLC $t_{R\ 1.13}$ min (analytical HPLC Method TS1). $^1$H NMR (499 MHz, CHLOROFORM-d) δ 7.50 (d, J=8.1 Hz, 1H), 7.19 (d, J=8.1 Hz, 1H), 2.51 (s, 3H), 2.34 (s, 3H), 1.34 (s, 12H).

Step 4: 5'-bromo-4-chloro-2,3-dimethyl-2'-nitro-1,1'-biphenyl

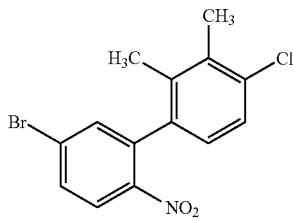
(26D)

To a solution of 4-bromo-2-iodo-1-nitrobenzene (753 mg, 2.30 mmol), 2-(4-chloro-2,3-dimethylphenyl)-4,4,5,5-tetramethyl-1,3,2-dioxaborolane (612 mg, 2.30 mmol), and Pd(Ph₃P)₄ (133 mg, 0.115 mmol) in 1,4-dioxane (15 mL) was added 2M aqueous potassium phosphate tribasic (3.44 mL, 6.88 mmol) and the biphasic mixture was degassed with nitrogen for 10 min. The vial was sealed and stirred at 100° C. for 17 h. Upon completion, the reaction mixture was cooled to room temperature. A duplicate reaction mixture of identical scale was run and then both reaction mixtures were combined. The material was concentrated and diluted with DCM and water. The organic layer was separated, and the aqueous layer was extracted twice with DCM. The combined organic layer was dried over sodium sulfate, filtered, and concentrated. The crude material was taken up in toluene and loaded onto silica gel for purification by silica gel column chromatography eluting with Hex/DCM 0-30% to obtain 11.59 g of 5'-bromo-4-chloro-2,3-dimethyl-2'-nitro-1,1'-biphenyl, contaminated with small amount byproducts. HPLC $t_R$ 1.22 min (analytical HPLC Method TS1). $^1$H NMR (499 MHz, CHLOROFORM-d) δ 7.89 (d, J=8.8 Hz, 1H), 7.66 (dd, J=8.8, 2.2 Hz, 1H), 7.46 (d, J=2.1 Hz, 1H), 7.26 (d, J=8.1 Hz, 1H), 6.87 (d, J=8.2 Hz, 1H), 2.39 (s, 3H), 2.05 (s, 3H).

Step 5: 6-bromo-2-chloro-3,4-dimethyl-9H-carbazole

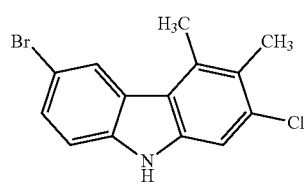
(26E)

To a solution of 5'-bromo-4-chloro-2,3-dimethyl-2'-nitro-1,1'-biphenyl (4.60 mmol) in o-dichlorobenzene (15 mL) was added triphenylphosphine (3.0 g, 11.5 mmol). The mixture was degassed with nitrogen gas, sealed, and heated to 180° C. for 14 h. Upon completion, the reaction mixture was cooled to room temperature and concentrated. The crude material was dissolved in DCM for loading onto silica gel for purification by silica gel column chromatography eluting with Hex/DCM 0-30% to obtain 6-bromo-2-chloro-3,4-dimethyl-9H-carbazole (537 mg, 1.74 mmol, 38.0% yield). HPLC $t_R$ 1.23 min (analytical HPLC Method TS1). $^1$H NMR (499 MHz, CHLOROFORM-d) δ 8.31 (d, J=1.8

Hz, 1H), 7.97 (br s, 1H), 7.50 (dd, J=8.5, 2.0 Hz, 1H), 7.35 (s, 1H), 7.30 (d, J=8.5 Hz, 1H), 2.82 (s, 3H), 2.51 (s, 3H).

Step 6: tent-butyl 5-(7-chloro-5,6-dimethyl-9H-carbazol-3-yl)-3,4-dihydropyridine-1(2H)-carboxylate

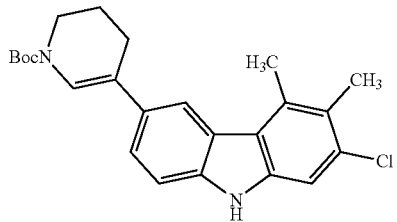

(26F)

To a solution of 6-bromo-2-chloro-3,4-dimethyl-9H-carbazole (100 mg, 0.324 mmol), tent-butyl 5-(4,4,5,5-tetramethyl-1,3,2-dioxaborolan-2-yl)-3,4-dihydropyridine-1(2H)-carboxylate (120 mg, 0.389 mmol), and PdCl$_2$(dppf) (11.9 mg, 0.016 mmol) in 1,4-dioxane (2.2 mL) was added aqueous potassium phosphate tribasic (2 M, 0.49 mL, 0.98 mmol). The biphasic mixture was degassed with nitrogen for 5 min. The mixture was sealed and stirred at 100° C. for 3 h. Upon completion, the reaction mixture was cooled to room temperature, concentrated, and loaded in DCM onto silica gel for purification by silica gel column chromatography eluting with 0-100% Hex/EtOAc to obtain tent-butyl 5-(7-chloro-5,6-dimethyl-9H-carbazol-3-yl)-3,4-dihydropyridine-1(2H)-carboxylate (111 mg, 0.270 mmol, 83% yield). LCMS m/z 411.5 (M+H)$^+$; HPLC $t_R$ 1.30 min (analytical HPLC Method TS1).

Step 7: tent-butyl 5-(7-(8-methoxy-[1,2,4]triazolo[1,5-a]pyridin-6-yl)-5,6-dimethyl-9H-carbazol-3-yl)-3,4-dihydropyridine-1(2H)-carboxylate

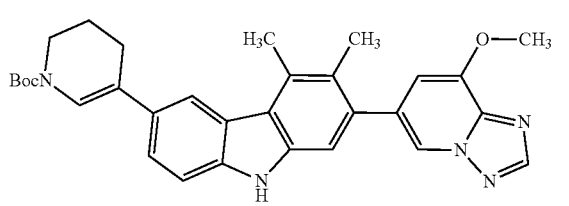

(26G)

To a solution of tent-butyl 5-(7-chloro-5,6-dimethyl-9H-carbazol-3-yl)-3,4-dihydropyridine-1(2H)-carboxylate (111 mg, 0.270 mmol), 8-methoxy-6-(4,4,5,5-tetramethyl-1,3,2-dioxaborolan-2-yl)-[1,2,4]triazolo[1,5-a]pyridine (97 mg, 0.351 mmol), and chloro(2-dicyclohexylphosphino-2'4'6'-triisopropyl-1,1'-biphenyl)[2-(2'-amino-1,1'-biphenyl)]palladium(II) (10.6 mg, 0.014 mmol) in 1,4-dioxane (1.8 mL) was added aqueous potassium phosphate tribasic (2 M, 0.41 mL, 0.820 mmol). The biphasic mixture was degassed with nitrogen for 5 min. The mixture was sealed and stirred at 70° C. for 3 h. Upon completion, the reaction mixture was cooled to room temperature, concentrated, taken up in DCM, and loaded onto silica gel for purification by silica gel column chromatography eluting with 0-100% Hex/EtOAc to obtain tent-butyl 5-(7-(8-methoxy-[1,2,4]triazolo[1,5-a]pyridin-6-yl)-5,6-dimethyl-9H-carbazol-3-yl)-3,4-dihydropyridine-1(2H)-carboxylate. Material was considered quantitative (0.270 mmol). LCMS m/z 524.6 (M+H)$^+$; HPLC $t_R$ 1.16 min (analytical HPLC Method TS1). $^1$H NMR (499 MHz, CHLOROFORM-d) δ 8.34 (s, 1H), 8.27-8.23 (m, 2H), 8.12 (br s, 1H), 7.47 (br d, J=8.1 Hz, 1H), 7.41 (br d, J=9.1 Hz, 1H), 7.29 (br s, 1H), 7.21 (s, 1H), 6.84 (d, J=1.1 Hz, 1H), 4.06 (s, 3H), 3.75-3.61 (m, 2H), 2.92 (br s, 3H), 2.62 (br t, J=5.9 Hz, 2H), 2.36 (s, 3H), 2.04 (s, 2H), 1.55 (s, 9H).

Step 8: Example 26

To a solution of tent-butyl 5-(7-(8-methoxy-[1,2,4]triazolo[1,5-a]pyridin-6-yl)-5,6-dimethyl-9H-carbazol-3-yl)-3,4-dihydropyridine-1(21/)-carboxylate (0.270 mmol) and triethylsilane (0.43 mL, 2.70 mmol) in DCM (2 mL) at 0° C. was added TFA (2 mL) slowly. After 45 minutes, the reaction mixture was concentrated. A portion of this material (1/7) was dissolved in MeOH for purification by preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 9-49% B over 20 minutes, then a 4-minute hold at 100% B; Flow: 20 mL/min. Fractions containing the product were combined and dried via centrifugal evaporation to obtain 2-(8-methoxy-[1,2,4]triazolo[1,5-a]pyridin-6-yl)-3,4-dimethyl-6-(piperidin-3-yl)-9H-carbazole (13.7 mg, 0.031 mmol, 81% yield). LCMS m/z 426.2 (M+H)$^+$; HPLC $t_R$ 1.27 min (analytical HPLC Method D). Select NMR peaks: $^1$H NMR (500 MHz, DMSO-d$_6$) δ 11.11 (br s, 1H), 8.47 (br s, 1H), 8.43 (s, 1H), 8.10 (s, 1H), 7.48 (d, J=8.3 Hz, 1H), 7.33 (br d, J=8.1 Hz, 1H), 7.30 (s, 1H), 7.04 (s, 1H), 4.02 (s, 3H), 2.85 (s, 3H), 2.32 (s, 3H).

Step 9: Example 27

To a portion of the material from Step 8 (1/7, 0.0386 mmol), N,N-dimethylglycine (15 mg, 0.145 mmol), and Et$_3$N (0.054 ml, 0.386 mmol) in DMF (1 mL) was added 2,4,6-tripropyl-1,3,5,2,4,6-trioxatriphosphorinane-2,4,6-trioxide (50% in DMF, 0.068 mL, 0.116 mmol) at room temperature. After stirring for 14 h, the reaction was quenched by the addition of water, 1.5 M aqueous K$_2$HPO$_4$, and DCM. The organic layer was separated and concentrated. The crude residue was taken up in DMF for purification by preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 11-51% B over 20 minutes, then a 4-minute hold at 100% B; Flow: 20 mL/min. Fractions containing the product were combined and dried via centrifugal evaporation to obtain 2-(dimethylamino)-1-(3-(7-(8-methoxy-[1,2,4]triazolo[1,5-a]pyridin-6-yl)-5,6-dimethyl-9H-carbazol-3-yl)piperidin-1-yl)ethan-1-one, TFA (5.8 mg, 9.08 μmol, 23.53% yield). LCMS m/z 511.4 (M+H)$^+$; HPLC $t_R$ 1.37 min (analytical HPLC Method D). Select NMR peaks: $^1$H NMR (500 MHz, DMSO-d$_6$) δ 11.08 (s, 1H), 8.47 (s, 1H), 8.43 (s, 1H), 8.12 (br d, J=19.4 Hz, 1H), 7.47 (br d, J=8.2 Hz, 1H), 7.41-7.31 (m, 1H), 7.30 (s, 1H), 7.05 (s, 1H), 4.02 (s, 3H), 2.32 (s, 3H).

Example 28

2-(8-methoxy-[1,2,4]triazolo[1,5-a]pyridin-6-yl)-3,4-dimethyl-6-(1-(tetrahydro-2H-pyran-4-yl)piperidin-3-yl)-9H-carbazole

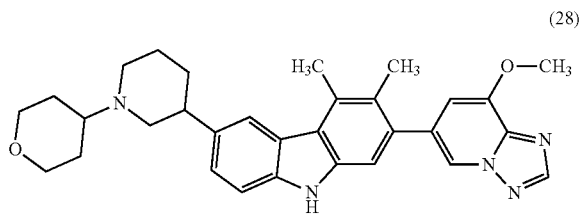 [SMILES: COc1cc(-c2cc3[nH]c4ccc(C5CCCN(C6CCOCC6)C5)cc4c3c(C)c2C)cn2ncnc12]

(28)

2-(8-Methoxy-[1,2,4]triazolo[1,5-a]pyridin-6-yl)-3,4-dimethyl-6-(piperidin-3-yl)-9H-carbazole (1/7, 0.0386 mmol) and Et$_3$N (0.027 mL, 0.193 mmol) were mixed in DMF (1 mL). Tetrahydro-4H-pyran-4-one (22 mg, 0.220 mmol) was added to the mixture vial followed by sodium triacetoxyborohydride (64 mg, 0.302 mmol) at room temperature. After stirring for 14 h, the reaction mixture was quenched by the addition of water, 1.5 M aqueous K$_2$HPO$_4$, and DCM. The organic layer was separated and concentrated. The crude residue was taken up in DMF for purification by preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-47% B over 25 minutes, then a 4-minute hold at 100% B; Flow: 20 mL/min. Fractions containing the product were combined and dried via centrifugal evaporation to obtain 2-(8-methoxy-[1,2,4]triazolo[1,5-a]pyridin-6-yl)-3,4-dimethyl-6-(1-(tetrahydro-2H-pyran-4-yl)piperidin-3-yl)-9H-carbazole (11.1 mg, 0.021 mmol, 54.6% yield). LCMS m/z 510.4 (M+H)$^+$; HPLC t$_R$ 1.30 min (analytical HPLC Method D). Select NMR peaks: $^1$h NMR (500 MHz, DMSO-d$_6$) δ 11.13 (br s, 1H), 8.51 (s, 1H), 8.45 (s, 1H), 8.08 (br s, 1H), 7.42 (br d, J=7.9 Hz, 1H), 7.30 (br d, J=8.5 Hz, 1H), 7.28 (br s, 1H), 7.06 (br s, 1H), 4.00 (s, 3H), 2.83 (br s, 3H), 2.31 (br s, 3H).

Example 29

6-(azetidin-3-yl)-2-(8-methoxy-[1,2,4]triazolo[1,5-a]pyridin-6-yl)-3,4-dimethyl-9H-carbazole

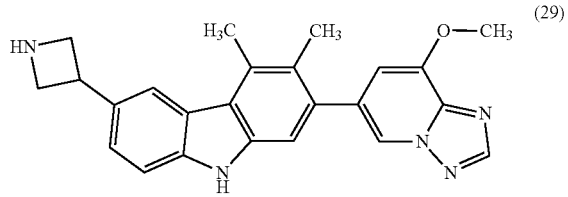 [SMILES: COc1cc(-c2cc3[nH]c4ccc(C5CNC5)cc4c3c(C)c2C)cn2ncnc12]

(29)

Example 30

2-(8-methoxy-[1,2,4]triazolo[1,5-a]pyridin-6-yl)-3,4-dimethyl-6-(1-(2-(methylsulfonyl)ethyl)azetidin-3-yl)-9H-carbazole

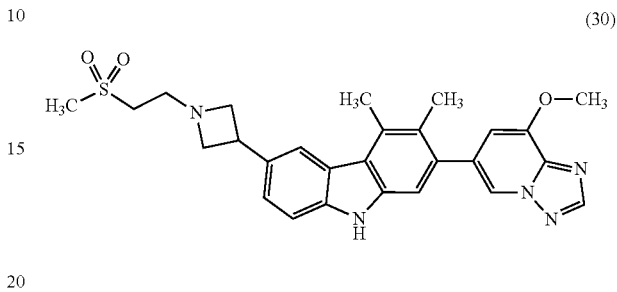

(30)

Step 1: tent-butyl 3-(7-chloro-5,6-dimethyl-9H-carbazol-3-yl)azetidine-1-carboxylate

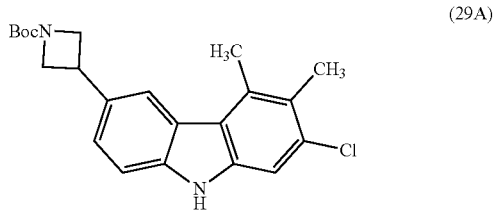 [SMILES: Cc1c(Cl)cc2[nH]c3ccc(C4CN(C(=O)OC(C)(C)C)C4)cc3c2c1C]

(29A)

6-Bromo-2-chloro-3,4-dimethyl-9H-carbazole (153 mg, 0.496 mmol), tert-butyl 3-iodoazetidine-1-carboxylate (281 mg, 0.992 mmol), tris(trimethylsilyl)silane (185 mg, 0.744 mmol), Ir(dF(CF$_3$)ppy)$_2$(dtbbpy)PF$_6$ (5.56 mg, 4.96 µmol), and Na$_2$CO$_3$ (210 mg, 1.98 mmol) were placed in a vial with a septum-lined cap and a stir bar. Next, 1,4-dioxane (8.3 mL) was added and the suspension was degassed with nitrogen for 5 minutes. To a separate vial was added nickel(II) chloride ethylene glycol dimethyl ether complex (5.45 mg, 0.025 mmol) and 4,4'-di-tent-butyl-2,2'-bipyridine (7.98 mg, 0.030 mmol), which was evacuated and backfilled with nitrogen followed by 1,4-dioxane (1.7 mL). This solution was degassed with nitrogen gas for 10 minutes and stirred. The resulting suspension was added to the reaction mixture and then the contents were degassed with nitrogen gas for another 10 minutes. The resulting suspension was irradiated with 34W KSH 150B Kessil blue grow lights (461 nm) with stirring for 16 h. Upon completion, the reaction mixture was filtered, concentrated, and purified on silica gel column chromatography loading the crude material in toluene and eluting the column with 0-100% Hex/DCM and then 0-50% EtOAc to obtain tent-butyl 3-(7-chloro-5,6-dimethyl-9H-carbazol-3-yl)azetidine-1-carboxylate (124 mg, 65% yield). LCMS m/z 329.0 (M−(tert-butyl)+H)$^+$; HPLC t$_R$ 1.18 min (analytical HPLC Method TS1).

Step 2: tent-butyl 3-(7-(8-methoxy-[1,2,4]triazolo[1,5-a]pyridin-6-yl)-5,6-dimethyl-9H-carbazol-3-yl)azetidine-1-carboxylate (29B)

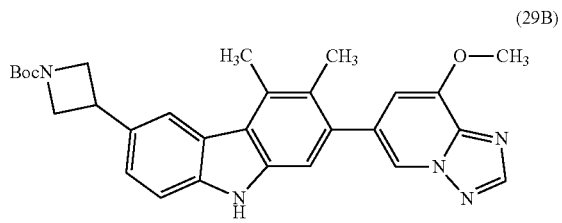 [SMILES: COc1cc(-c2cc3[nH]c4ccc(C5CN(C(=O)OC(C)(C)C)C5)cc4c3c(C)c2C)cn2ncnc12]

To a solution of tent-butyl 3-(7-chloro-5,6-dimethyl-9H-carbazol-3-yl)azetidine-1-carboxylate (124 mg, 0.322 mmol), 8-methoxy-6-(4,4,5,5-tetramethyl-1,3,2-dioxaborolan-2-yl)-[1,2,4]triazolo[1,5-a]pyridine (115 mg, 0.419 mmol), and chloro(2-dicyclohexylphosphino-2'4'6'-triisopropyl-1,1'-bipheyl)[2-(2'-amino-1,1'-biphenyl)]palladium (II) (12.67 mg, 0.016 mmol) in 1,4-dioxane (2.2 mL) was added aqueous potassium phosphate tribasic (2M, 0.48 mL, 0.96 mmol) and the biphasic mixture was degassed with nitrogen for 5 min. The mixture was sealed and stirred at 70° C. for 3 h. Upon completion, the reaction mixture was concentrated, dissolved in DCM and loaded onto silica gel for purification by silica gel column chromatography eluting with 0-100% Hex/EtOAc to obtain tent-butyl 3-(7-(8-methoxy-[1,2,4]triazolo[1,5-a]pyridin-6-yl)-5,6-dimethyl-9H-carbazol-3-yl)azetidine-1-carboxylate. LCMS m/z 498.6 (M+H)$^+$; HPLC $t_R$ 1.06 min (analytical HPLC Method TS1). $^1$H NMR (499 MHz, CHLOROFORM-d) δ 8.46 (s, 1H), 8.34 (s, 1H), 8.25-8.23 (m, 1H), 8.15 (s, 1H), 7.47-7.42 (m, 2H), 7.22 (s, 1H), 6.83 (d, J=1.2 Hz, 1H), 4.44 (t, J=8.6 Hz, 2H), 4.15-4.06 (m, 2H), 4.04 (s, 3H), 3.99-3.91 (m, 1H), 2.90 (s, 3H), 2.36 (s, 3H), 1.51 (s, 9H).

Step 3: Example 29

To a solution of tent-butyl 3-(7-(8-methoxy-[1,2,4]triazolo[1,5-a]pyridin-6-yl)-5,6-dimethyl-9H-carbazol-3-yl)azetidine-1-carboxylate (0.215 mmol) in DCM (2 mL) was added TFA (1 mL) at room temperature. After stirring for 10 min, the reaction mixture was concentrated to obtain tent-butyl 3-(7-(8-methoxy-[1,2,4]triazolo[1,5-a]pyridin-6-yl)-5,6-dimethyl-9H-carbazol-3-yl)azetidine-1-carboxylate, TFA (0.215 mmol). LCMS m/z 398.6 (M+H)$^+$; HPLC $t_R$ 0.64 min (analytical HPLC Method TS1).

Step 4: Example 30

A portion (1/6) of the material from Step 3, 6-(azetidin-3-yl)-2-(8-methoxy-[1,2,4]triazolo[1,5-a]pyridin-6-yl)-3,4-dimethyl-9H-carbazole, TFA (0.0358 mmol), was dissolved in DMF (1 mL). Et$_3$N (0.025 mL, 0.179 mmol) and 1-bromo-2-(methylsulfonyl)ethane (8.0 mg, 0.043 mmol) were added sequentially. The reaction mixture was stirred for 2 h, and then another aliquot each of Et$_3$N (0.075 mL, 0.537 mmol) and 1-bromo-2-(methylsulfonyl) ethane (24 mg, 0.128 mmol) was added. The reaction mixture was stirred for 1.5 h more, and then diluted with a few drops of water and DMF for purification by preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 13-53% B over 20 minutes, then a 4-minute hold at 100% B; Flow: 20 mL/min. Fractions containing the product were combined and dried via centrifugal evaporation to obtain 2-(8-methoxy-[1,2,4]triazolo[1,5-a]pyridin-6-yl)-3,4-dimethyl-6-(1-(2-(methylsulfonyl)ethyl)azetidin-3-yl)-9H-carbazole (15.7 mg, 0.031 mmol, 87% yield). LCMS m/z 504.2 (M+H)$^+$; HPLC $t_R$ 1.45 min (analytical HPLC Method D). $^1$H NMR (500 MHz, DMSO-d$_6$) δ 11.19 (s, 1H), 8.54 (s, 1H), 8.46 (s, 1H), 8.14 (s, 1H), 7.51-7.42 (m, 2H), 7.29 (s, 1H), 7.08 (s, 1H), 4.01 (s, 3H), 3.84-3.77 (m, 1H), 3.77-3.70 (m, 2H), 3.29-3.21 (m, 2H), 3.18 (br t, J=6.7 Hz, 2H), 3.09 (s, 3H), 2.89 (br t, J=6.6 Hz, 2H), 2.84 (s, 3H), 2.32 (s, 3H).

The Examples in Table 4 were prepared using a similar procedure used to prepare Example 30.

TABLE 4

| Ex. No. | Structure | Mol Wt | LCMS m/z obs. | HPLC $t_R$ (min) | HPLC method |
|---|---|---|---|---|---|
| 31 | 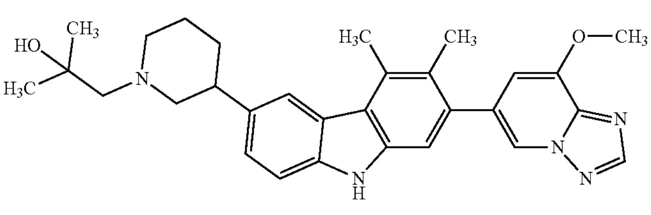 [SMILES: COc1cc(-c2cc3[nH]c4ccc(C5CCCN(CC(C)(C)O)C5)cc4c3c(C)c2C)cn2ncnc12] | 497.6 | 498.4 | 1.39 | QC-ACN-AA-XB |
| 32 | 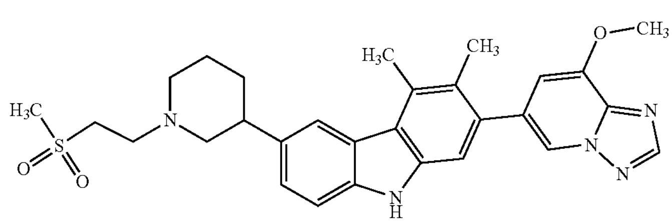 [SMILES: COc1cc(-c2cc3[nH]c4ccc(C5CCCN(CCS(C)(=O)=O)C5)cc4c3c(C)c2C)cn2ncnc12] | 531.7 | 532.4 | 1.65 | QC-ACN-AA-XB |

TABLE 4-continued

| Ex. No. | Structure | Mol Wt | LCMS m/z obs. | HPLC $t_R$ (min) | HPLC method |
|---|---|---|---|---|---|
| 33 | 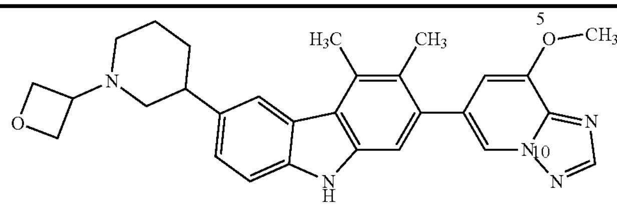 | 481.6 | 482.2 | 1.24 | QC-ACN-TFA-XB |
| 34 | 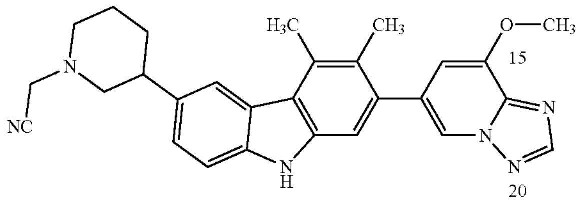 | 464.6 | 465.3 | 1.39 | QC-ACN-TFA-XB |
| 35 | 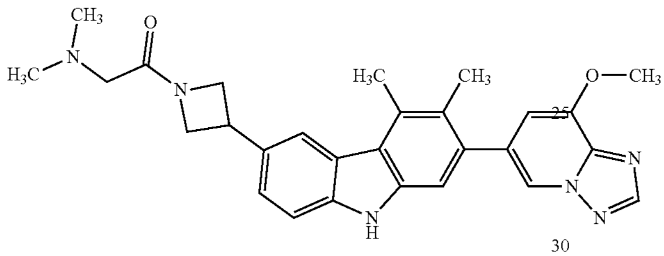 | 482.6 | 483.3 | 1.15 | QC-ACN-TFA-XB |
| 36 | 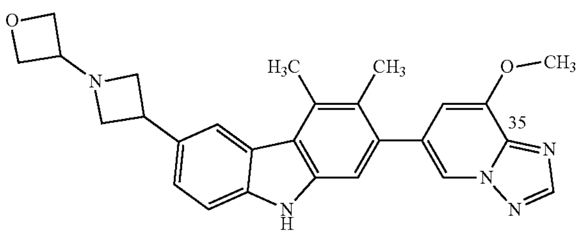 [SMILES: COc1cc(-c2cc3[nH]c4ccc(C5CN(C6COC6)C5)cc4c3c(C)c2C)cn2ncnc12] | 453.5 | 454.3 | 1.41 | QC-ACN-AA-XB |
| 37 | 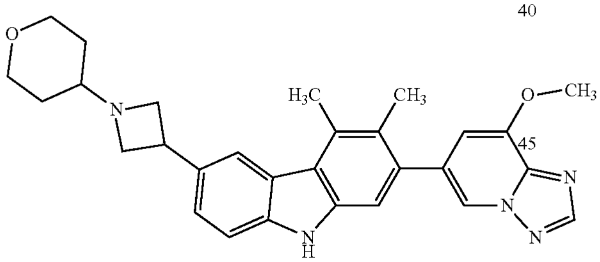 | 481.6 | 482.4 | 1.24 | QC-ACN-AA-XB |
| 38 | 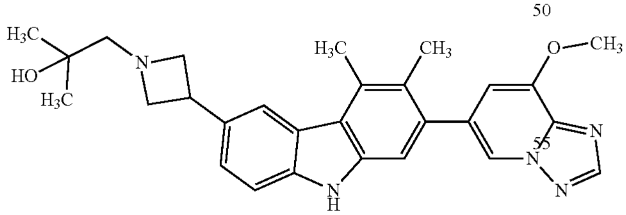 | 469.6 | 470.3 | 1.18 | QC-ACN-AA-XB |
| 39 | 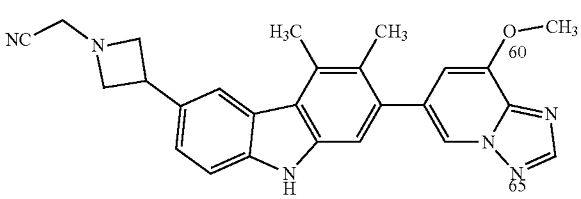 [SMILES: COc1cc(-c2cc3[nH]c4ccc(C5CN(CC#N)C5)cc4c3c(C)c2C)cn2ncnc12] | 436.5 | 437.2 | 1.63 | QC-ACN-AA-XB |

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-KB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 µM. After a 30 minute compound pre-treatment at room temperature, the cells are then stimulated with a TLR7 ligand (gardiquimod at a final concentration of 7.5 µM), TLR8 ligand (R848 at a final concentration of 15.9 µM) or TLR9 ligand (ODN2006 at a final concentration of 5 nM) to activate NF-κB and AP-1 which induce the production of SEAP. After a 22 h incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 5

TLR7/8/9 Reporter Assay Data

| Ex. No. | TLR7 $IC_{50}$ nM | TLR8 $IC_{50}$ nM | TLR9 $IC_{50}$ nM |
|---|---|---|---|
| 1 | 651 | 209 | 1060 |
| 2 | 22 | 103 | 53 |
| 3 | 109 | 358 | 668 |
| 4 | 1475 | 1801 | 541 |
| 5 | 16 | 29 | 182 |
| 6 | >3125 | >3125 | 1055 |
| 7 | >3125 | >3125 | 1057 |
| 8 | 1376 | 861 | 648 |
| 9 | 383 | 61 | 302 |
| 10 | 2.2 | 2.4 | 350 |
| 11 | 2.4 | 21 | 40 |
| 12 | 1.4 | 6.8 | 153 |
| 13 | 0.7 | 6.8 | 349 |
| 14 | 1.2 | 1.4 | 318 |
| 15 | 0.8 | 0.8 | 95 |
| 16 | 35 | 5.5 | 158 |
| 17 | 1.9 | 1.4 | 108 |
| 18 | 3.2 | 0.9 | 650 |
| 19 | 1.8 | 4.0 | 416 |
| 20 | 1.9 | 2.1 | 224 |
| 21 | 1.5 | 12 | 60 |
| 22 | 1.6 | 0.7 | 342 |
| 23 | 4.1 | 0.9 | 259 |
| 24 | 68 | 1.5 | 388 |
| 25 | 1.8 | 0.4 | 264 |
| 26 | 1.3 | 1.6 | 271 |
| 27 | 3.3 | 3.8 | 1171 |
| 28 | 7.8 | 0.7 | 523 |
| 29 | 3.1 | 1.0 | 228 |
| 30 | 5.5 | 1.0 | 813 |
| 31 | 8.1 | 1.2 | 587 |
| 32 | 9.4 | 2.0 | 802 |
| 33 | 15.5 | 2.2 | 1231 |
| 34 | 1.3 | 2.5 | 321 |
| 35 | 4.5 | 3.3 | 845 |
| 36 | 5.6 | 1.8 | 861 |
| 37 | 5.2 | 1.3 | 1051 |
| 38 | 2.5 | 0.4 | 514 |
| 39 | 11 | 4.0 | 1236 |

What is claimed is:

1. A compound of Formula (I),

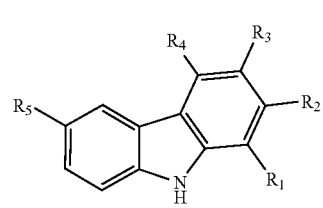

or a salt thereof, wherein:

R is H, R, or —OR;

$R_2$ is —NHC(O)$CH_3$, or a cyclic group selected from:

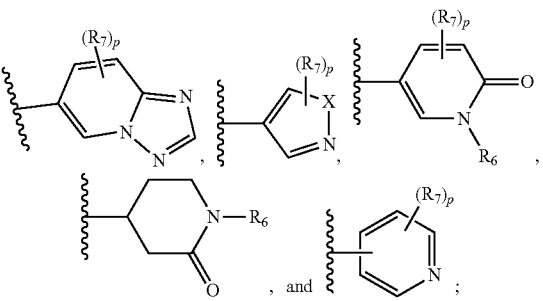

$R_3$ and $R_4$ are independently H, R, or –OR;
each R is independently $C_{1-3}$ alkyl;
$R_5$ is:

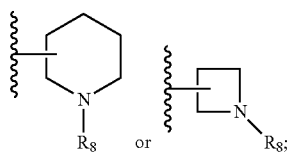

$R_6$ is H or $C_{1-3}$ alkyl;
each $R_7$ is independently $C_{1-3}$ alkyl or $C_{1-3}$ alkoxy;
$R_8$ is H, —$CH_2$CN, —$CH_2$C($CH_3$)$_2$OH, —C(O)$CH_2$N($CH_3$)$_2$, —$CH_2CH_2$S(O)$_2CH_3$, oxetanyl, or tetrahydropyranyl; and
p is zero, 1 or 2.

2. The compound according to claim 1, or a salt thereof, wherein $R_2$ is:

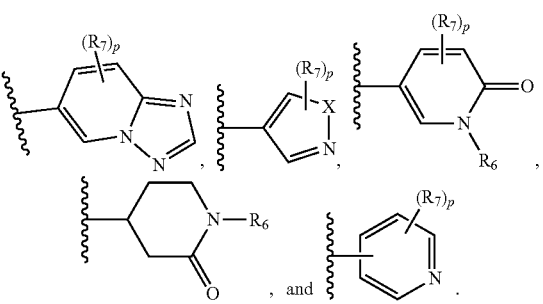

3. The compound according to claim 1, or a salt thereof, wherein

R$_1$ is H;

R$_2$ is: —NHC(O)CH$_3$, or a cyclic group selected from:

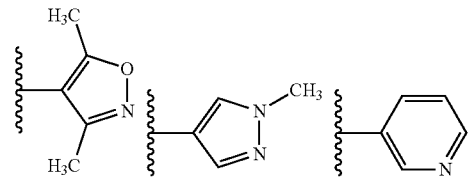

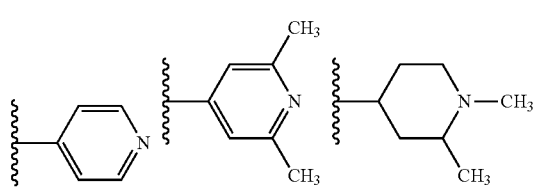

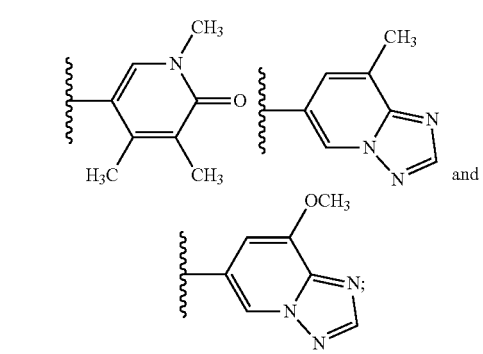

R$_3$ is H or —CH$_3$;
R$_4$ is H or —CH$_3$;
R$_5$ is:

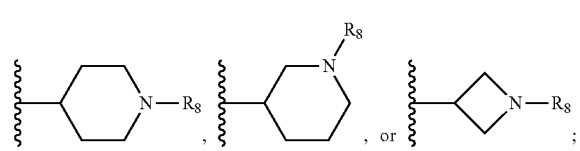

and

R$_8$ is hydrogen, —CH$_2$CN, —CH$_2$C(CH$_3$)$_2$OH, —C(O)CH$_2$N(CH$_3$)$_2$, —CH$_2$CH$_2$S(O)$_2$CH$_3$, oxetanyl, or tetrahydropyranyl.

4. The compound according to claim 1, or a salt thereof, wherein X is O.

5. The compound according to claim 1, or a salt thereof, wherein X is —NR.

6. The compound according to claim 1, or a salt thereof, wherein R$_4$ is H.

7. The compound according to claim 1, or a salt thereof, wherein R$_4$ is C$_{1-3}$ alkyl.

8. The compound according to claim 1, or a salt thereof, wherein R is —CH$_3$.

9. The compound according to claim 1, or a salt thereof, wherein R$_5$ is:

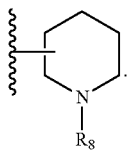

10. The compound according to claim 1, or a salt thereof, wherein R$_5$ is:

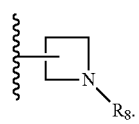

11. The compound according to claim 1, or a salt thereof, wherein said compound is:

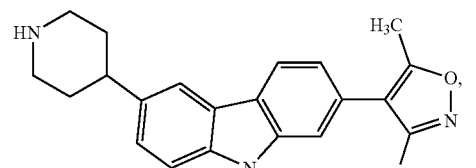

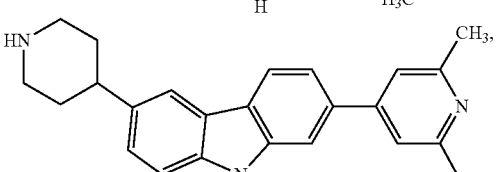

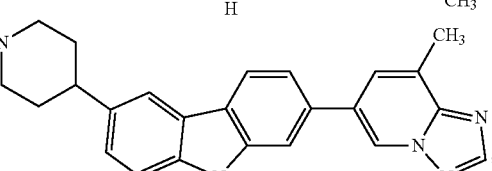

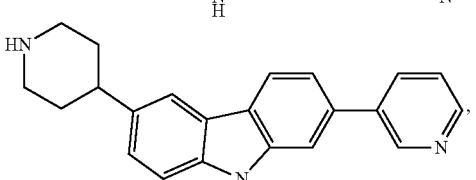

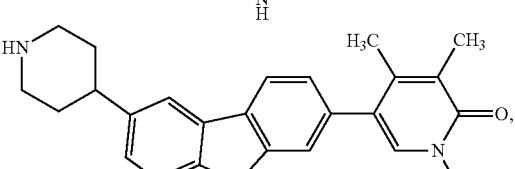

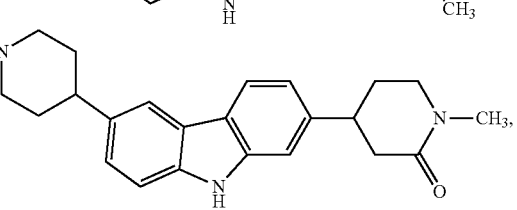

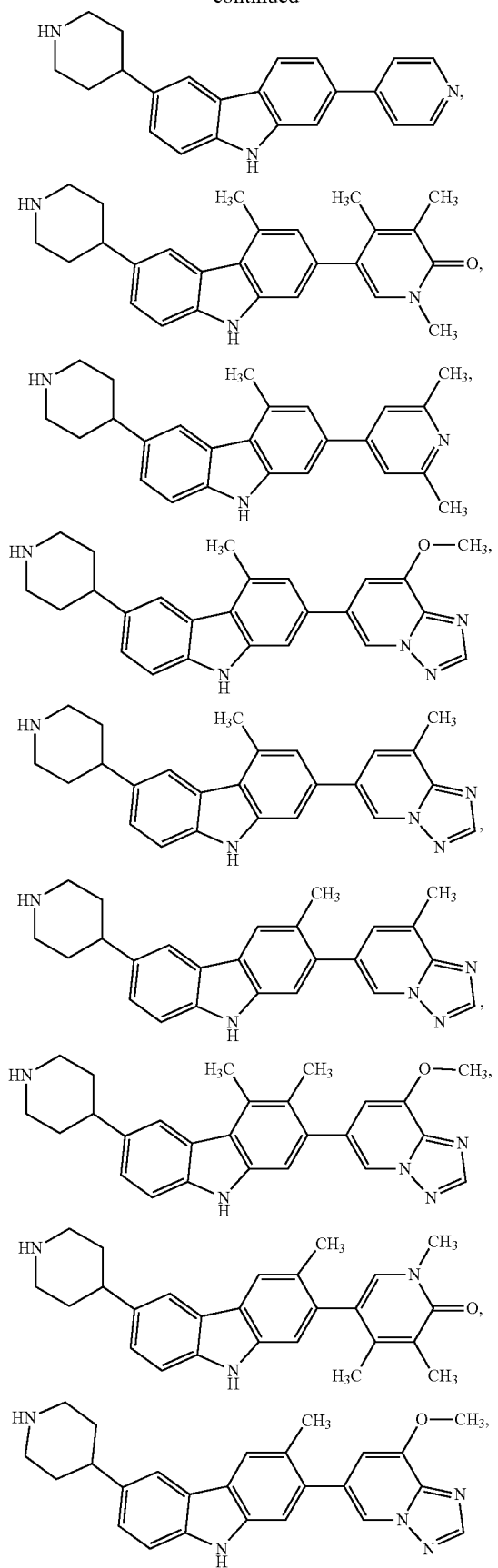
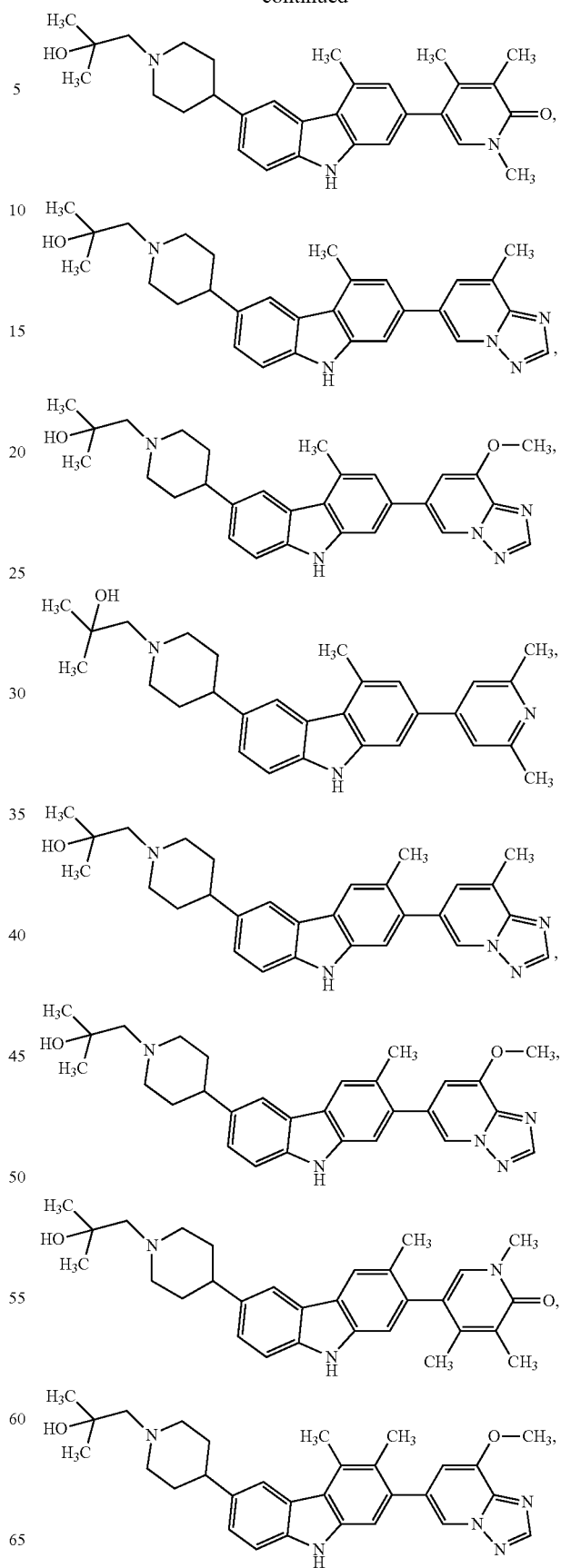

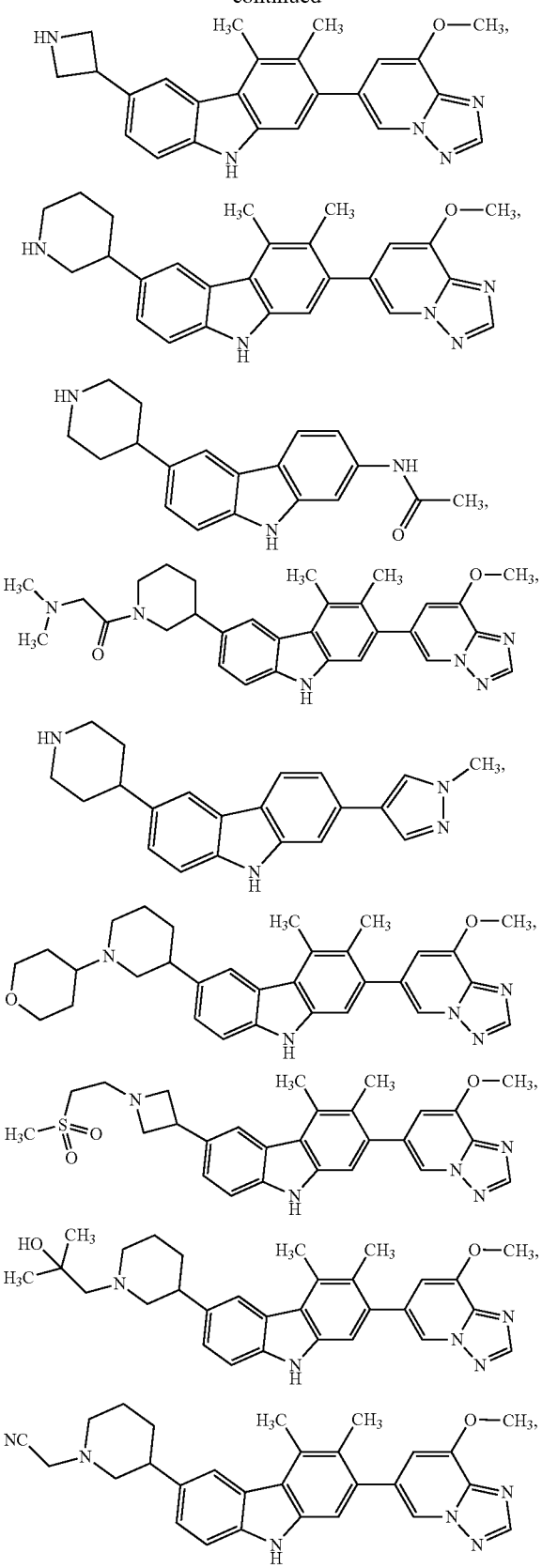

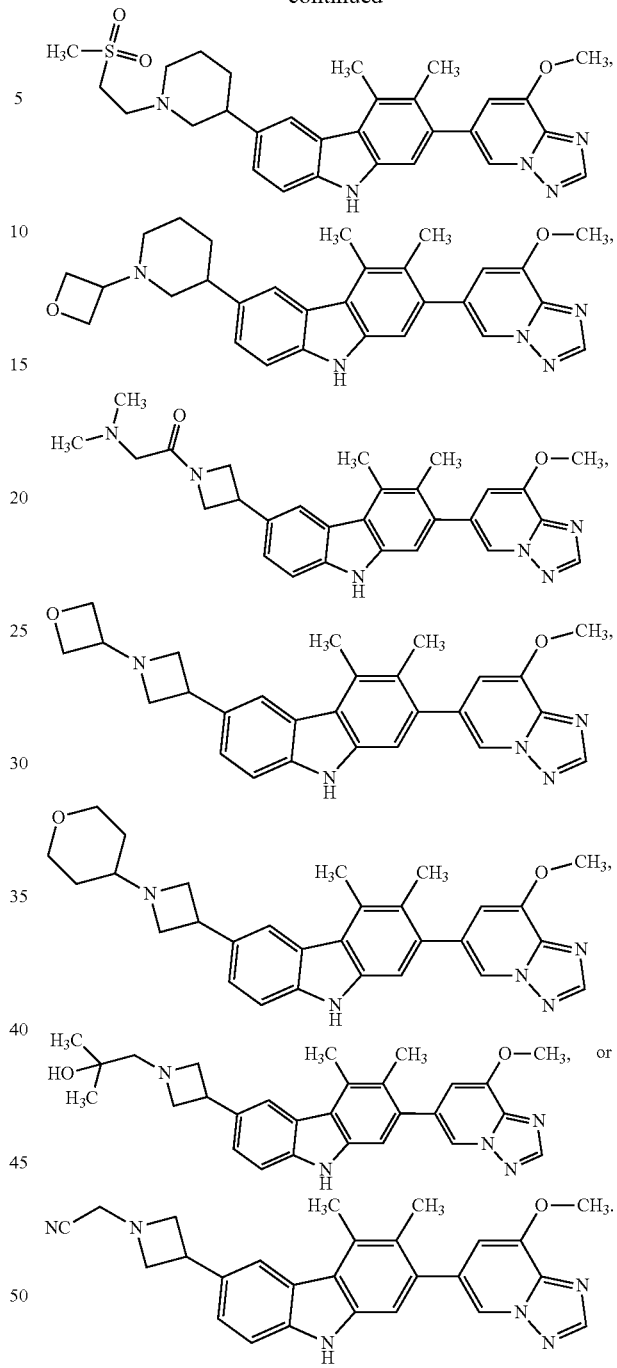

12. A pharmaceutical composition comprising a compound according to claim 1, or a salt thereof, and a pharmaceutically acceptable carrier.

13. A method of treating an autoimmune disease or a chronic inflammatory disease, comprising administering to a mammalian patient a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

* * * * *

UNITED STATES PATENT AND TRADEMARK OFFICE
CERTIFICATE OF CORRECTION

PATENT NO.         : 12,384,760 B2
APPLICATION NO.    : 17/766392
DATED              : August 12, 2025
INVENTOR(S)        : Dharmpal Dodd et al.

Page 1 of 1

It is certified that error appears in the above-identified patent and that said Letters Patent is hereby corrected as shown below:

In the Claims

Column 72
Claim 1, Line 15, "R" should read -- R1 --.

Column 72
Claim 1, Line 31, insert -- X is O, –NH, or –NR; -- above "R3 and R4 are independently H, R, or –OR;".

Signed and Sealed this
Third Day of February, 2026

John A. Squires
*Director of the United States Patent and Trademark Office*